(12) United States Patent
Thompson et al.

(10) Patent No.: US 8,153,831 B2
(45) Date of Patent: Apr. 10, 2012

(54) ORGANOMETALLIC COMPOUNDS, PROCESSES FOR THE PREPARATION THEREOF AND METHODS OF USE THEREOF

(75) Inventors: David M. Thompson, East Amherst, NY (US); David Walter Peters, Kingsland, TX (US); Scott Houston Meiere, Williamsville, NY (US)

(73) Assignee: Praxair Technology, Inc., Danbury, CT (US)

( * ) Notice: Subject to any disclaimer, the term of this patent is extended or adjusted under 35 U.S.C. 154(b) by 1028 days.

(21) Appl. No.: 11/900,382

(22) Filed: Sep. 11, 2007

(65) Prior Publication Data

US 2008/0081127 A1 Apr. 3, 2008

Related U.S. Application Data

(60) Provisional application No. 60/847,653, filed on Sep. 28, 2006.

(51) Int. Cl.
*C07F 11/00* (2006.01)
*C07F 9/00* (2006.01)
*C23C 16/00* (2006.01)

(52) U.S. Cl. ............... 556/58; 556/42; 556/43; 556/59; 556/60; 427/255.394; 427/569; 438/99

(58) Field of Classification Search ............. 556/58, 556/59, 60, 42, 43; 427/255.394, 569; 438/99
See application file for complete search history.

(56) References Cited

U.S. PATENT DOCUMENTS 6,491,978 B1 12/2002 Kalyanam
2005/0215805 A1 9/2005 Meiere

OTHER PUBLICATIONS

Miyake et al., Angew. Chem. Int. Ed. Engl., vol. 7, No. 11, pp. 880-881 (1968).*
Nolan et al., Journal of Organometallic Chemistry, vol. 282, No. 2, pp. 357-362 (1985).*
Eilbracht, P. et al., "Metallinduzierte CC-Einfachbindungsspaltung 5,5-dialkylsubstituierter Cyclopentadiene durch Metallcarbonylkomplexe der 6. Nebengruppe", Chem. Ber. 113, 1033-1046 (1980), XP-002468402.

Green, M. et al., "Synthesis of the W≡W Triply Bonded Dimers $[W_2(\eta-C_5H_4R)_2X_4]$ (X = Cl, R = Me or $Pr^i$; X = Br, R = $Pr^1$) and X-Ray Crystal Structures of $[W(\eta-C_5H_4Pr^i)Cl4]$ and $[W_2(\eta-C_5H_4Pr^i)_2Cl_4]$", J. Chem. Soc. Dalton Trans., pp. 3793-3800 (1990).
Chi, Y. et al., "Synthesis of the First Cluster Complexes Bearing Three Quadruply Bridging CO Ligands: X-ray Crystal Structure of [C5H3(SiMe3)2]WRu6(μ3-H)-(CO)18", J. Am. Chem. Soc. 119, 11114-11115 (1997).
Bitterwolf, Thomas E. et al., "Dihydrogen as a Reactant in the Photochemistry of Bimetallic Cyclopentadienyl Carbonyl Compounds", Organometallics 19, 4915-4917 (2000).
Fischer, E. O. "Cyclopentadienyl Tricarbonyl Hydrides of Chromium, Molybdenum, and Tungsten." Inorganic Syntheses, Chapter 38, pp. 136-139, (1963).
Hampden-Smith, M. and Kodas, T. "3 Chemical Vapor Deposition of Tungsten", The Chemistry of Metal CVD, Weinheim, New York. Basel, Cambridge VCH, 1994. ISBN 3-527-29071-0. pp. 138-148.
Kim, Do_Heyoung et al. "Characteristics of Tungsten Carbide Films Prepared by Plasmaw-Assisted ALD Using Bis (tert-butylimido) bis (dimethylamido)tungsten". Journal of the Electrochemical Society, 150 (10) (2003) pp. C740-C744.
Laine, Richard M. "The Photochemical Synthesis of (Cyclooctatetraene) $W(CO)_4$." Transition Met. Chem. 5, (1980) pp. 158-159.
Leigh, G. J. and Fischer, E. O. "The Reactions of Cyclooctadienes with the Hexacarbonyls of Group VI Transition Elements." Journal of Organometallic Chemistry 4 (1965) pp. 461-465.

* cited by examiner

*Primary Examiner* — Porfirio Nazario Gonzalez
(74) *Attorney, Agent, or Firm* — Nilay S. Dalel; Iurie A. Schwartz

(57) ABSTRACT

This invention relates to organometallic compounds represented by the formula $(L_1)_yM(L_2)_{z-y}$ wherein M is a Group 5 metal or a Group 6 metal, $L_1$ is a substituted or unsubstituted anionic 6 electron donor ligand, $L_2$ is the same or different and is (i) a substituted or unsubstituted anionic 2 electron donor ligand, (ii) a substituted or unsubstituted cationic 2 electron donor ligand, or (iii) a substituted or unsubstituted neutral 2 electron donor ligand; y is an integer of 1, and z is the valence of M; and wherein the sum of the oxidation number of M and the electric charges of $L_1$ and $L_2$ is equal to 0; a process for producing the organometallic compounds; and a method for depositing a metal and/or metal carbide/nitride layer, e.g., a tungsten, tungsten nitride, tungsten carbide, or tungsten carbonitride layer, on a substrate by the thermal or plasma enhanced dissociation of the organometallic precursor compounds, e.g., by CVD or ALD techniques. The metal and/or metal carbide layer is useful as a liner or barrier layer for conducting metals and high dielectric constant materials in integrated circuit manufacturing.

29 Claims, No Drawings

ORGANOMETALLIC COMPOUNDS,
PROCESSES FOR THE PREPARATION
THEREOF AND METHODS OF USE
THEREOF

RELATED APPLICATIONS

This application claims the benefit of U.S. Provisional Application Ser. No. 60/847,653, filed Sep. 28, 2006, which is incorporated herein by reference.

FIELD OF THE INVENTION

This invention relates to organometallic compounds, a process for producing organometallic compounds, and a method for producing a film or coating from organometallic precursor compounds.

BACKGROUND OF THE INVENTION

The semiconductor industry is currently considering the use of thin films of various metals for a variety of applications. Many organometallic complexes have been evaluated as potential precursors for the formation of these thin films. A need exists in the industry for developing new compounds and for exploring their potential as precursors for film depositions. The industry movement from physical vapor deposition (PVD) to chemical vapor deposition (CVD) and atomic layer deposition (ALD) processes, due to the increased demand for higher uniformity and conformality in thin films, has lead to a demand for suitable precursors for future semiconductor materials.

In the industry, conducting metals such as copper are being used to fill sub-micron features on substrates during the manufacture of integrated circuits. However, copper can diffuse into the structure of adjacent dielectric layers, thereby compromising the integrity of the devices being formed. Diffusion, as well as interlayer defects, such as layer delamination, may be prevented by depositing a barrier layer, a liner layer, or a combination of both, on the underlying material before depositing the conducting metal. The barrier layer is deposited on the underlying material and is often a nitride of a metal that prevents interlayer diffusion and minimizes chemical reactions between underlying materials and subsequently deposited materials. The liner layer is conventionally composed of a metal that provides adhesion for the conducting metal layer.

Metals such as tungsten, tantalum, niobium, and the respective metal nitrides are being considered for liner and barrier materials in copper applications. See, for example, U.S. Pat. Nos. 6,491,978 B1 and 6,379,748 B1. Depending on the application, a liner adhesion layer and/or a diffusion barrier layer may comprise a metal, such as tungsten, tantalum, or niobium, a metal nitride layer, such as tungsten nitride, tantalum nitride, or niobium nitride layer, a metal and metal nitride stack, or other combinations of diffusion barrier materials. Metal and metal nitride layers have been traditionally deposited by PVD techniques. However, traditional PVD techniques are not well suited for providing conformal coverage on the wall and bottom surfaces of high aspect ratio vias and other features. Therefore, as aspect ratios increase and device features shrink, new precursors and deposition techniques are being investigated to provide conformal coverage in these device features.

As referred to above, one proposed alternative to PVD techniques of metal and metal nitride layers is depositing the layers by CVD techniques to provide good conformal coverage of substrate features. The ability to deposit conformal metal and metal nitride layers in high aspect ratio features by the dissociation of organometallic precursors has gained interest in recent years due to the development of CVD techniques. In such techniques, an organometallic precursor comprising a metal component and organic component is introduced into a processing chamber and dissociates to deposit the metal component on a substrate while the organic portion of the precursor is exhausted from the chamber.

There are few commercially available organometallic precursors for the deposition of metal layers, such as tungsten, tantalum, and niobium precursors by CVD techniques. The precursors that are available produce layers which may have unacceptable levels of contaminants such as carbon and oxygen, and have less than desirable diffusion resistance, low thermal stability, and undesirable layer characteristics. Further, in some cases, the available precursors used to deposit metal nitride layers produce layers with high resistivity, and in some cases, produce layers that are insulative.

Another proposed alternative to PVD processes is ALD processes. ALD technology is considered superior to PVD technology in depositing thin films. However, the challenge for ALD technology is availability of suitable precursors. ALD deposition process involves a sequence of steps. The steps include 1) adsorption of precursors on the surface of substrate; 2) purging off excess precursor molecules in gas phase; 3) introducing reactants to react with precursor on the substrate surface; and 4) purging off excess reactant.

For ALD processes, the precursor should meet stringent requirements. First, the ALD precursors should be able to form a monolayer on the substrate surface either through physisorption or chemisorption under the deposition conditions. Second, the adsorbed precursor should be stable enough to prevent premature decomposition on the surface to result in high impurity levels. Third, the adsorbed molecule should be reactive enough to interact with reactants to leave a pure phase of the desirable material on the surface at relatively low temperature.

As with CVD, there are few commercially available organometallic precursors for the deposition of metal layers, such as tungsten, tantalum, and niobium precursors by ALD techniques. ALD precursors that are available may have one or more of following disadvantages: 1) low vapor pressure, 2) wrong phase of the deposited material, and 3) high carbon incorporation in the film.

Therefore, there remains a need for developing new compounds and for exploring their potential as CVD and ALD precursors for film depositions. There also remains a need for a process for forming liner and/or barrier layers of metal or metal derivative materials from organometallic precursors using CVD and ALD techniques. Ideally, the liner and/or barrier layers deposited are substantially free of contaminants, have reduced layer resistivities, improved interlayer adhesion, improved diffusion resistance, and improved thermal stability over those produced with PVD processes.

SUMMARY OF THE INVENTION

This invention relates in part to organometallic compounds represented by the formula $(L_1)_y M(L_2)_{z-y}$, wherein M is a Group 5 metal or a Group 6 metal, $L_1$ is a substituted or unsubstituted anionic 6 electron donor ligand, $L_2$ is the same or different and is (i) a substituted or unsubstituted anionic 2 electron donor ligand, (ii) a substituted or unsubstituted cationic 2 electron donor ligand, or (iii) a substituted or unsubstituted neutral 2 electron donor ligand; $y$ is an integer of 1, and $z$ is the valence of M; and wherein the sum of the oxidation number of M and the electric charges of $L_1$ and $L_2$ is equal to 0. Typically, M is selected from tungsten (W), tantalum (Ta), molybdenum (Mo), niobium (Nb), vanadium (V) or chromium (Cr), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, and $L_2$ is selected from (i) substituted or unsubstituted anionic 2 electron donor ligands such as hydrido, halo and an alkyl group having from 1 to 12 carbon atoms (e.g., methyl, ethyl and the like), (ii) substituted or unsubstituted cationic 2 electron donor ligands such as nitrosyl, and (iii) substituted or unsubstituted neutral 2 electron donor ligands such as carbonyl, phosphino, amino, alkenyl, alkynyl, nitrile (e.g., acetonitrile) and isonitrile.

This invention also relates in part to organometallic compounds represented by the formula $L_1M''(L_3)_x(L_4)_y(L_5)_{z'}$ wherein M" is a Group 6 metal having an oxidation state of $\underline{n}$, $L_1$ is a substituted or unsubstituted anionic 6 electron donor ligand, $L_3$ is the same or different and is a substituted or unsubstituted cationic 2 electron donor ligand, $L_4$ is the same or different and is a substituted or unsubstituted neutral 2 electron donor ligand, $L_5$ is the same or different and is a substituted or unsubstituted anionic 2 electron donor ligand; n is an integer of 0 or 2, z' is an integer of 0 or 1, x is an integer equal to $z'-n+1$ provided that x is greater than or equal to 0, and y' is an integer equal to $7\underline{n}/2+2x-4z'$ provided that y' is greater than or equal to 0; and wherein the sum of the oxidation number of M" and the electric charges of $L_1$, $L_3$, $L_4$ and $L_5$ is equal to 0. Typically, M" is selected from tungsten (W), molybdenum (Mo), or chromium (Cr), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, $L_3$ is selected from substituted or unsubstituted cationic 2 electron donor ligands such as nitrosyl, $L_4$ is selected from substituted or unsubstituted neutral 2 electron donor ligands such as carbonyls, phosphines, amines, nitriles, and alkenes, and $L_5$ is selected from substituted or unsubstituted anionic 2 electron donor ligands such as hydrido, halo and an alkyl groups having from 1 to 12 carbon atoms (e.g., methyl, ethyl and the like).

This invention further relates in part to organometallic compounds represented by the formula $(L_1)_yM(CO)_{x'}(L_6)_{z-y-x'}$ wherein M is a Group 5 metal or a Group 6 metal, $L_1$ is a substituted or unsubstituted anionic 6 electron donor ligand, $L_6$ is the same or different and is (i) a substituted or unsubstituted anionic 2 electron donor ligand, or (ii) a substituted or unsubstituted cationic 2 electron donor ligand; x' is an integer of from 0 to 3, y is an integer of 1, and z is the valence of M; and wherein the sum of the oxidation number of M and the electric charges of $L_1$, $L_6$ and CO groups is equal to 0. Typically, M is selected from tungsten (W), tantalum (Ta), molybdenum (Mo), niobium (Nb), vanadium (V) or chromium (Cr), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, and $L_6$ is selected from (i) substituted or unsubstituted anionic 2 electron donor ligands such as hydrido, halo and an alkyl group having from 1 to 12 carbon atoms (e.g., methyl, ethyl and the like), and (ii) substituted or unsubstituted cationic 2 electron donor ligands such as nitrosyl.

This invention yet further relates in part to organometallic compounds represented by the formula $L_1M'L_4(L_5)_3$ wherein M' is a Group 5 metal, $L_1$ is a substituted or unsubstituted anionic 6 electron donor ligand, $L_4$ is a substituted or unsubstituted neutral 2 electron donor ligand, and $L_5$ is the same or different and is a substituted or unsubstituted anionic 2 electron donor ligand; and wherein the sum of the oxidation number of M' and the electric charges of $L_1$, $L_4$ and $L_5$ is equal to 0. Typically, M' is selected from tantalum (Ta), niobium (Nb) and vanadium (V), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, $L_4$ is selected from substituted or unsubstituted neutral 2 electron donor ligands such as carbonyls, phosphines, amines, nitriles, and alkenes, and $L_5$ is selected from substituted or unsubstituted anionic 2 electron donor ligands such as hydrido, halo and an alkyl groups having from 1 to 12 carbon atoms (e.g., methyl, ethyl and the like).

This invention also relates in part to organometallic compounds represented by the formula $L_1M'L_3(L_4)_2$ wherein M' is a Group 5 metal, $L_1$ is a substituted or unsubstituted anionic 6 electron donor ligand, $L_3$ is a substituted or unsubstituted cationic 2 electron donor ligand, and $L_4$ is the same or different and is a substituted or unsubstituted neutral 2 electron donor ligand; and wherein the sum of the oxidation number of M' and the electric charges of $L_1$, $L_3$ and $L_4$ is equal to 0. Typically, M' is selected from tantalum (Ta), niobium (Nb) and vanadium (V), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, $L_3$ is selected from substituted or unsubstituted cationic 2 electron donor ligands such as nitrosyls, and $L_4$ is selected from substituted or unsubstituted neutral 2 electron donor ligands such as carbonyls, phosphines, amines, nitriles, and alkenes.

This invention further relates in part to organometallic compounds represented by the formula $(L_1)_yM(NO)_{x''}(L_7)_{z-y-x''}$ wherein M is a Group 5 metal or a Group 6 metal, $L_1$ is a substituted or unsubstituted anionic 6 electron donor ligand, $L_7$ is the same or different and is (i) a substituted or unsubstituted anionic 2 electron donor ligand, or (ii) a substituted or unsubstituted neutral 2 electron donor ligand; x" is an integer of from 0 to 2, y is an integer of 1, and z is the valence of M; and wherein the sum of the oxidation number of M and the electric charges of $L_1$, $L_7$ and NO groups is equal to 0. Typically, M is selected from tungsten (W), tantalum (Ta), molybdenum (Mo), niobium (Nb), vanadium (V) or chromium (Cr), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, and $L_7$ is selected from (i) substituted or unsubstituted anionic 2 electron donor ligands such as hydrido, halo and an alkyl group having from 1 to 12 carbon atoms (e.g., methyl, ethyl and the like), and (ii) substituted or unsubstituted neutral 2 electron donor ligands such as carbonyl, phosphino, amino, alkenyl, alkynyl, nitrile (e.g., acetonitrile) and isonitrile.

This invention yet further relates in part to organometallic compounds represented by the formula $L_1M'(L_3)_2L_5$ wherein M' is a Group 5 metal, $L_1$ is a substituted or unsubstituted anionic 6 electron donor ligand, $L_3$ is the same or different and is a substituted or unsubstituted cationic 2 electron donor ligand, and $L_5$ is a substituted or unsubstituted anionic 2 electron donor ligand; and wherein the sum of the oxidation number of M' and the electric charges of $L_1$, $L_3$ and $L_5$ is equal to 0. Typically, M' is selected from tantalum (Ta), niobium (Nb) and vanadium (V), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, $L_3$ is selected from substituted or unsubstituted cationic 2 electron donor ligands such as nitrosyls, and $L_5$ is selected from substituted or unsubstituted anionic 2 electron donor ligands such as hydrido, halo and an alkyl groups having from 1 to 12 carbon atoms (e.g., methyl, ethyl and the like).

This invention also relates in part to organometallic compounds represented by the formula $(L_8)_y M(L_4)_{z-y}$ wherein M is a Group 5 metal or a Group 6 metal, $L_4$ is the same or different and is a substituted or unsubstituted neutral 2 electron donor ligand, $L_8$ is a substituted chelated diene ligand, $y$ is an integer of 1, and $z$ is the valence of M; and wherein the sum of the oxidation number of M and the electric charges of $L_4$ and $L_8$ is equal to 0. Typically, M is selected from tungsten (W), tantalum (Ta), molybdenum (Mo), niobium (Nb), vanadium (V) or chromium (Cr), $L_4$ is selected from substituted or unsubstituted neutral 2 electron donor ligands such as carbonyl, phosphino, amino, alkenyl, alkynyl, nitrile (e.g., acetonitrile) and isonitrile, and $L_8$ is selected from substituted chelated diene ligands such as alkyl substituted 1,4-cyclohexadienyl, alkyl substituted 1,3-cyclopentadienyl, alkyl substituted 1,5-cycloheptadienyl, and alkyl substituted 1,6-cyclooctadienyl.

This invention further relates in part to organometallic compounds represented by the formula $(L_8)M''(L_4)_4$ wherein M'' is a Group 6 metal, $L_4$ is the same or different and is a substituted or unsubstituted neutral 2 electron donor ligand, and $L_8$ is a substituted chelated diene ligand; and wherein the sum of the oxidation number of M'' and the electric charges of $L_4$ and $L_8$ is equal to 0. Typically, M'' is selected from tungsten (W), molybdenum (Mo), or chromium (Cr), $L_4$ is selected from substituted or unsubstituted neutral 2 electron donor ligands such as carbonyls, phosphines, amines, alkenes, alkynes, nitriles (e.g., acetonitrile) and isonitriles, and $L_8$ is selected from substituted chelated diene ligands such as alkyl substituted 1,4-cyclohexadiene, alkyl substituted 1,3-cyclopentadiene, alkyl substituted 1,5-cycloheptadiene, and alkyl substituted 1,6-cyclooctadiene.

This invention also relates in part to organometallic precursors represented by the formulae above.

This invention further relates in part to a process for producing the compounds represented by the formulae above, for example, a compound having the formula $(L_1)_y M(L_2)_{z-y}$, wherein M is a Group 5 metal or a Group 6 metal, $L_1$ is a substituted or unsubstituted anionic 6 electron donor ligand, $L_2$ is the same or different and is (i) a substituted or unsubstituted anionic 2 electron donor ligand, (ii) a substituted or unsubstituted cationic 2 electron donor ligand, or (iii) a substituted or unsubstituted neutral 2 electron donor ligand; $y$ is an integer of 1, and $z$ is the valence of M; and wherein the sum of the oxidation number of M and the electric charges of $L_1$ and $L_2$ is equal to 0, which process comprises reacting a metal halide, a salt and a reducing agent in the presence of a first solvent and under reaction conditions sufficient to produce an intermediate reaction material, and reacting said intermediate reaction material with a base material in the presence of a second solvent and under reaction conditions sufficient to produce said compound.

This invention yet further relates in part to a method for producing a film, coating or powder by decomposing an organometallic precursor, said organometallic precursor represented by the formulae above, for example, an organometallic precursor having the formula $(L_1)_y M(L_2)_{z-y}$ wherein M is a Group 5 metal or a Group 6 metal, $L_1$ is a substituted or unsubstituted anionic 6 electron donor ligand, $L_2$ is the same or different and is (i) a substituted or unsubstituted anionic 2 electron donor ligand, (ii) a substituted or unsubstituted cationic 2 electron donor ligand, or (iii) a substituted or unsubstituted neutral 2 electron donor ligand; $y$ is an integer of 1, and $z$ is the valence of M; and wherein the sum of the oxidation number of M and the electric charges of $L_1$ and $L_2$ is equal to 0, thereby producing said film, coating or powder.

This invention also relates in part to a method for processing a substrate in a processing chamber, said method comprising (i) introducing an organometallic precursor into said processing chamber, said organometallic precursor represented by the formulae above, for example, an organometallic precursor having the formula $(L_1)_y M(L_2)_{z-y}$ wherein M is a Group 5 metal or a Group 6 metal, $L_1$ is a substituted or unsubstituted anionic 6 electron donor ligand, $L_2$ is the same or different and is (i) a substituted or unsubstituted anionic 2 electron donor ligand, (ii) a substituted or unsubstituted cationic 2 electron donor ligand, or (iii) a substituted or unsubstituted neutral 2 electron donor ligand; $y$ is an integer of 1, and $z$ is the valence of M; and wherein the sum of the oxidation number of M and the electric charges of $L_1$ and $L_2$ is equal to 0, (ii) heating said substrate to a temperature of about 100° C. to about 400° C., and (iii) dissociating said organometallic precursor in the presence of a processing gas to deposit a metal layer on said substrate.

This invention further relates in part to a method for forming a metal material on a substrate from an organometallic precursor, said method comprising vaporizing said organometallic precursor to form a vapor, and contacting the vapor with the substrate to form said metal material thereon, wherein the organometallic precursor is represented by the formulae above, for example, an organometallic precursor represented by the formula $(L_1)_y M(L_2)_{z-y}$ wherein M is a Group 5 metal or a Group 6 metal, $L_1$ is a substituted or unsubstituted anionic 6 electron donor ligand, $L_2$ is the same or different and is (i) a substituted or unsubstituted anionic 2 electron donor ligand, (ii) a substituted or unsubstituted cationic 2 electron donor ligand, or (iii) a substituted or unsubstituted neutral 2 electron donor ligand; $y$ is an integer of 1, and $z$ is the valence of M; and wherein the sum of the oxidation number of M and the electric charges of $L_1$ and $L_2$ is equal to 0.

This invention yet further relates in part to a method of fabricating a microelectronic device structure, said method comprising vaporizing an organometallic precursor represented by the formulae above, for example, an organometallic precursor having the formula $(L)_y M(L_1)_{z-y}$ wherein M is a Group 5 metal or a Group 6 metal, L is a substituted or unsubstituted anionic ligand, $L_1$ is the same or different and is hydrogen or a substituted or unsubstituted hydrocarbon or heteroatom-containing ligand, $y$ is an integer of 1, and $z$ is the valence of M, to form a vapor, an contacting said vapor with a substrate to deposit a metal-containing film on the substrate, and thereafter metallizing the substrate with copper or integrating it with a ferroelectric thin film.

The invention has several advantages. For example, the method of the invention is useful in generating organometallic compound precursors that have varied chemical structures and physical properties. Films generated from the organometallic compound precursors can be deposited with a short incubation time, and the films deposited from the organometallic compound precursors exhibit good smoothness.

A preferred embodiment of this invention is that the organometallic precursor compounds may be liquid at room temperature. In some situations, liquids may be preferred over solids from an ease of semiconductor process integration perspective.

For CVD and ALD applications, the organometallic precursors of this invention can exhibit an ideal combination of thermal stability, vapor pressure, and reactivity with the intended substrates for semiconductor applications. The organometallic precursors of this invention can desirably exhibit liquid state at delivery temperature, and/or tailored ligand spheres that can lead to better reactivity with semiconductor substrates. All of the organometallic precursors of this invention avoid the use of halide based ligands.

DETAILED DESCRIPTION OF THE INVENTION

As indicated above, this invention relates to organometallic precursor compounds capable of forming metal-based materials, e.g., a metal and metal carbide/nitride such as tungsten, tungsten nitride, tungsten carbide, or tungsten carbonitride, on a substrate by techniques such as CVD and ALD. The substrate can preferably be microelectronic device structures for applications such as copper metallization of semiconductor device structures.

The organometallic precursor compounds of this invention useful for the formation of metal-based material layers, e.g., tungsten, tungsten nitride, tungsten carbide, or tungsten carbonitride barrier layers, include those compounds represented by the formulae above, for example, an organometallic precursor having the formula $(L_1)_y M(L_2)_{z-y}$ wherein M is a Group 5 metal or a Group 6 metal, e.g., tungsten (W), tantalum (Ta), molybdenum (Mo), niobium (Nb), vanadium (V) or chromium (Cr), $L_1$ is a substituted or unsubstituted anionic 6 electron donor ligand, e.g., cyclopentadienyl, cycloheptadienyl, pentadienyl, pyrrolyl, imidazolyl, pyrazolyl and boratabenzyl, $L_2$ is the same or different and is (i) a substituted or unsubstituted anionic 2 electron donor ligand such as hydrido, halo and an alkyl group having from 1 to 12 carbon atoms (e.g., methyl, ethyl and the like), (ii) a substituted or unsubstituted cationic 2 electron donor ligand such as nitrosyl, or (iii) a substituted or unsubstituted neutral 2 electron donor ligand such as carbonyl, phosphino, amino, alkenyl, alkynyl, nitrile (e.g., acetonitrile) and isonitrile; y is an integer of 1, and z is the valence of M; and wherein the sum of the oxidation number of M and the electric charges of $L_1$ and $L_2$ is equal to 0. For example, $L_2$ can be hydrogen or a substituted or unsubstituted hydrocarbon or heteroatom-containing ligand.

In an embodiment, when M is tungsten, the organometallic compounds of this invention include the following: (i) M is tungsten (W) with a (+2) oxidation number, $L_1$ is a substituted or unsubstituted anionic 6 electron donor ligand with a (−1) electrical charge, one $L_2$ ligand is a substituted or unsubstituted anionic 2 electron donor ligand with a (−1) electrical charge, and the remaining three $L_2$ ligands are the same or different and are each a substituted or unsubstituted neutral 2 electron donor ligand with a zero (0) electrical charge; (ii) M is tungsten (W) with a (0) oxidation number, $L_1$ is a substituted or unsubstituted anionic 6 electron donor ligand with a (−1) electrical charge, one $L_2$ ligand is a substituted or unsubstituted cationic 2 electron donor ligand with a (+1) electrical charge, and the remaining two $L_2$ ligands are the same or different and are each a substituted or unsubstituted neutral 2 electron donor ligand with a zero (0) electrical charge; and (iii) M is tungsten (W) with a (0) oxidation number, $L_1$ is a substituted or unsubstituted anionic 6 electron donor ligand with a (−1) electrical charge, one $L_2$ ligand is a substituted or unsubstituted anionic 2 electron donor ligand with a (−1) electrical charge, and the remaining two $L_2$ ligands are the same or different and are each a substituted or unsubstituted cationic 2 electron donor ligand with a (+1) electrical charge. For all of the above organometallic compounds, the sum of the oxidation number of M and the electric charges of $L_1$ and $L_2$ is equal to 0.

Other organometallic precursor compounds of this invention useful for the formation of metal-based material layers, e.g., tungsten, tungsten nitride, tungsten carbide, or tungsten carbonitride barrier layers, include those compounds having the formula $L_1 M''(L_3)_x (L_4)_y (L_5)_{z'}$ wherein M" is a Group 6 metal having an oxidation state of n, $L_1$ is a substituted or unsubstituted anionic 6 electron donor ligand, $L_3$ is the same or different and is a substituted or unsubstituted cationic 2 electron donor ligand, $L_4$ is the same or different and is a substituted or unsubstituted neutral 2 electron donor ligand, $L_5$ is the same or different and is a substituted or unsubstituted anionic 2 electron donor ligand; n is an integer of 0 or 2, z' is an integer of 0 or 1, x is an integer equal to z'−n+1 provided that x is greater than or equal to 0, and y' is an integer equal to 7n/2+2x−4z' provided that y' is greater than or equal to 0; and wherein the sum of the oxidation number of M" and the electric charges of $L_1$, $L_3$, $L_4$ and $L_5$ is equal to 0. Typically, M" is selected from tungsten (W), molybdenum (Mo), or chromium (Cr), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, $L_3$ is selected from substituted or unsubstituted cationic 2 electron donor ligands such as nitrosyl, $L_4$ is selected from substituted or unsubstituted neutral 2 electron donor ligands such as carbonyls, phosphines, amines, nitriles, and alkenes, and $L_5$ is selected from substituted or unsubstituted anionic 2 electron donor ligands such as hydrido, halo and an alkyl groups having from 1 to 12 carbon atoms (e.g., methyl, ethyl and the like). For example, $L_3$, $L_4$ and $L_5$, as appropriate, can be hydrogen or a substituted or unsubstituted hydrocarbon or heteroatom-containing ligand.

Other organometallic precursor compounds of this invention useful for the formation of metal-based material layers, e.g., tungsten, tungsten nitride, tungsten carbide, or tungsten carbonitride barrier layers, include those compounds having the formula $(L_1)_y M(CO)_{x'} (L_6)_{z-y-x'}$ wherein M is a Group 5 metal or a Group 6 metal, $L_1$ is a substituted or unsubstituted anionic 6 electron donor ligand, $L_6$ is the same or different and is (i) a substituted or unsubstituted anionic 2 electron donor ligand, or (ii) a substituted or unsubstituted cationic 2 electron donor ligand; x' is an integer of from 0 to 3, y is an integer of 1, and z is the valence of M; and wherein the sum of the oxidation number of M and the electric charges of $L_1$, $L_6$ and CO groups is equal to 0. Typically, M is selected from tungsten (W), tantalum (Ta), molybdenum (Mo), niobium (Nb), vanadium (V) or chromium (Cr), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, and $L_6$ is selected from (i) substituted or unsubstituted anionic 2 electron donor ligands such as hydrido, halo and an alkyl group having from 1 to 12 carbon atoms (e.g., methyl, ethyl and the like), and (ii) substituted or unsubstituted cationic 2 electron donor ligands such as nitrosyl. For example, $L_6$ can be hydrogen or a substituted or unsubstituted hydrocarbon or heteroatom-containing ligand.

Other organometallic precursor compounds of this invention useful for the formation of metal-based material layers, e.g., tungsten, tungsten nitride, tungsten carbide, or tungsten carbonitride barrier layers, include those compounds having the formula $L_1 M' L_4 (L_5)_3$ wherein M' is a Group 5 metal, $L_1$ is a substituted or unsubstituted anionic 6 electron donor ligand, $L_4$ is a substituted or unsubstituted neutral 2 electron donor ligand, and $L_5$ is the same or different and is a substituted or unsubstituted anionic 2 electron donor ligand; and wherein the sum of the oxidation number of M' and the electric charges of $L_1$, $L_4$ and $L_5$ is equal to 0. Typically, M' is selected from tantalum (Ta), niobium (Nb) and vanadium (V), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, $L_4$ is selected from substituted or unsubstituted neutral 2 electron donor ligands such as carbonyls, phosphines, amines, nitriles, and alkenes, and $L_5$ is selected from substituted or unsubstituted anionic 2 electron donor ligands such as hydrido, halo and an alkyl groups having from 1 to 12 carbon atoms (e.g., methyl, ethyl and the like). For example, $L_4$ and $L_5$, as appropriate, can be hydrogen or a substituted or unsubstituted hydrocarbon or heteroatom-containing ligand.

Other organometallic precursor compounds of this invention useful for the formation of metal-based material layers, e.g., tungsten, tungsten nitride, tungsten carbide, or tungsten carbonitride barrier layers, include those compounds having the formula $L_1M'L_3(L_4)_2$ wherein M' is a Group 5 metal, $L_1$ is a substituted or unsubstituted anionic 6 electron donor ligand, $L_3$ is a substituted or unsubstituted cationic 2 electron donor ligand, and $L_4$ is the same or different and is a substituted or unsubstituted neutral 2 electron donor ligand; and wherein the sum of the oxidation number of M' and the electric charges of $L_1$, $L_3$ and $L_4$ is equal to 0. Typically, M' is selected from tantalum (Ta), niobium (Nb) and vanadium (V), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, $L_3$ is selected from substituted or unsubstituted cationic 2 electron donor ligands such as nitrosyls, and $L_4$ is selected from substituted or unsubstituted neutral 2 electron donor ligands such as carbonyls, phosphines, amines, nitriles, and alkenes. For example, $L_3$ and $L_4$, as appropriate, can be a substituted or unsubstituted hydrocarbon or heteroatom-containing ligand.

Other organometallic precursor compounds of this invention useful for the formation of metal-based material layers, e.g., tungsten, tungsten nitride, tungsten carbide, or tungsten carbonitride barrier layers, include those compounds having the formula $(L_1)_yM(NO)_{x''}(L_7)_{z-y-x''}$ wherein M is a Group 5 metal or a Group 6 metal, $L_1$ is a substituted or unsubstituted anionic 6 electron donor ligand, $L_7$ is the same or different and is (i) a substituted or unsubstituted anionic 2 electron donor ligand, or (ii) a substituted or unsubstituted neutral 2 electron donor ligand; x" is an integer of from 0 to 2, y is an integer of 1, and z is the valence of M; and wherein the sum of the oxidation number of M and the electric charges of $L_1$, $L_7$ and NO groups is equal to 0. Typically, M is selected from tungsten (W), tantalum (Ta), molybdenum (Mo), niobium (Nb), vanadium (V) or chromium (Cr), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, and $L_7$ is selected from (i) substituted or unsubstituted anionic 2 electron donor ligands such as hydrido, halo and an alkyl group having from 1 to 12 carbon atoms (e.g., methyl, ethyl and the like), and (ii) substituted or unsubstituted neutral 2 electron donor ligands such as carbonyl, phosphino, amino, alkenyl, alkynyl, nitrile (e.g., acetonitrile) and isonitrile. For example, $L_7$ can be hydrogen or a substituted or unsubstituted hydrocarbon or heteroatom-containing ligand.

Other organometallic precursor compounds of this invention useful for the formation of metal-based material layers, e.g., tungsten, tungsten nitride, tungsten carbide, or tungsten carbonitride barrier layers, include those compounds having the formula $L_1M'(L_3)_2L_5$ wherein M' is a Group 5 metal, $L_1$ is a substituted or unsubstituted anionic 6 electron donor ligand, $L_3$ is the same or different and is a substituted or unsubstituted cationic 2 electron donor ligand, and $L_5$ is a substituted or unsubstituted anionic 2 electron donor ligand; and wherein the sum of the oxidation number of M' and the electric charges of $L_1$, $L_3$ and $L_5$ is equal to 0. Typically, M' is selected from tantalum (Ta), niobium (Nb) and vanadium (V), $L_1$ is selected from substituted or unsubstituted anionic 6 electron donor ligands such as cyclopentadienyl, cycloheptadienyl, pentadienyl, pyrrolyl, imidazolyl, pyrazolyl and boratabenzyl, $L_3$ is selected from substituted or unsubstituted cationic 2 electron donor ligands such as nitrosyls, and $L_5$ is selected from substituted or unsubstituted anionic 2 electron donor ligands such as hydrido, halo and an alkyl groups having from 1 to 12 carbon atoms (e.g., methyl, ethyl and the like). For example, $L_3$ and $L_5$ can be, as appropriate, hydrogen or a substituted or unsubstituted hydrocarbon or heteroatom-containing ligand.

Other organometallic precursor compounds of this invention useful for the formation of metal-based material layers, e.g., tungsten, tungsten nitride, tungsten carbide, or tungsten carbonitride barrier layers, include those compounds having the formula $(L_8)_yM(L_4)_{z-y}$ wherein M is a Group 5 metal or a Group 6 metal, $L_4$ is the same or different and is a substituted or unsubstituted neutral 2 electron donor ligand, $L_8$ is a substituted chelated diene ligand, y is an integer of 1, and z is the valence of M; and wherein the sum of the oxidation number of M and the electric charges of $L_4$ and $L_8$ is equal to 0. Typically, M is selected from tungsten (W), tantalum (Ta), molybdenum (Mo), niobium (Nb), vanadium (V) or chromium (Cr), $L_4$ is selected from substituted or unsubstituted neutral 2 electron donor ligands such as carbonyl, phosphino, amino, alkenyl, alkynyl, nitrile (e.g., acetonitrile) and isonitrile, and $L_8$ is selected from substituted chelated diene ligands such as alkyl substituted 1,4-cyclohexadienyl, alkyl substituted 1,3-cyclopentadienyl, alkyl substituted 1,5-cycloheptadienyl, and alkyl substituted 1,6-cyclooctadienyl. For example, $L_4$ can be a substituted or unsubstituted hydrocarbon or heteroatom-containing ligand.

Other organometallic precursor compounds of this invention useful for the formation of metal-based material layers, e.g., tungsten, tungsten nitride, tungsten carbide, or tungsten carbonitride barrier layers, include those compounds having the formula $(L_8)M''(L_4)_4$ wherein M" is a Group 6 metal, $L_4$ is the same or different and is a substituted or unsubstituted neutral 2 electron donor ligand, and $L_8$ is a substituted chelated diene ligand; and wherein the sum of the oxidation number of M" and the electric charges of $L_4$ and $L_8$ is equal to 0. Typically, M" is selected from tungsten (W), molybdenum (Mo), or chromium (Cr), $L_4$ is selected from substituted or unsubstituted neutral 2 electron donor ligands such as carbonyls, phosphines, amines, alkenes, alkynes, nitriles (e.g., acetonitrile) and isonitriles, and $L_8$ is selected from substituted chelated diene ligands such as alkyl substituted 1,4-cyclohexadiene, alkyl substituted 1,3-cyclopentadiene, alkyl substituted 1,5-cycloheptadiene, and alkyl substituted 1,6-cyclooctadiene. For example, $L_4$ can be a substituted or unsubstituted hydrocarbon or heteroatom-containing ligand.

This invention in part provides organometallic precursors and a method of processing a substrate to form a metal-based material layer, e.g., tungsten, tungsten nitride, tungsten carbide, or tungsten carbonitride layer, on the substrate by CVD or ALD of the organometallic precursor. The metal-based material layer is deposited on a heated substrate by thermal or plasma enhanced dissociation of the organometallic precursor having the formulae above in the presence of a processing gas. The processing gas may be an inert gas, such as helium and argon, and combinations thereof. The composition of the processing gas is selected to deposit metal-based material layers, e.g., tungsten, tungsten nitride, tungsten carbide, or tungsten carbonitride layers, as desired.

For the organometallic precursors of this invention represented by the formulae above, M, M' and M" represent the metal to be deposited. Examples of metals which can be deposited according to this invention are the Group 6 metals of tungsten, molybdenum and chromium, and the Group 5 metals of vanadium, tantalum, and niobium. The letter z represents the valence of the metal, M, of the precursor, with a valence of 6 for the Group 6 metals and a valence of 5 for the Group 5 metals.

Illustrative substituted and unsubstituted anionic ligands ($L_1$) useful in this invention include, for example, 6 electron anionic donor ligands such as cyclopentadienyl (Cp), cycloheptadienyl, pentadienyl, pyrrolyl, boratabenzyl, pyrazolyl, imidazolyl, and the like. Cp is a cyclopentadienyl ring having the general formula ($C_5H_5^-$) which forms a ligand with the metal, M. The cyclopentadienyl ring may be substituted, thereby having the formula (Cp(R')). The precursor contains one 6 electron anionic donor ligand group, e.g., cyclopentadienyl group.

Other illustrative substituted and unsubstituted 6 electron anionic donor ligands include cyclodienyl complexes, e.g., cyclohexadienyl, cycloheptadienyl, cyclooctadienyl rings, heterocyclic rings, aromatic rings, such as substituted cyclopentadienyl ring like ethylcyclopentadienyl, and others, as known in the art.

Permissible substituents of the substituted anionic, cationic and neutral ligands used herein include halogen atoms, acyl groups having from 1 to about 12 carbon atoms, alkoxy groups having from 1 to about 12 carbon atoms, alkoxycarbonyl groups having from 1 to about 12 carbon atoms, alkyl groups having from 1 to about 12 carbon atoms, amine groups having from 1 to about 12 carbon atoms or silyl groups having from 0 to about 12 carbon atoms.

Illustrative halogen atoms include, for example, fluorine, chlorine, bromine and iodine. Preferred halogen atoms include chlorine and fluorine.

Illustrative acyl groups include, for example, formyl, acetyl, propionyl, butyryl, isobutyryl, valeryl, 1-methylpropylcarbonyl, isovaleryl, pentylcarbonyl, 1-methylbutylcarbonyl, 2-methylbutylcarbonyl, 3-methylbutylcarbonyl, 1-ethylpropylcarbonyl, 2-ethylpropylcarbonyl, and the like. Preferred acyl groups include formyl, acetyl and propionyl.

Illustrative alkoxy groups include, for example, methoxy, ethoxy, n-propoxy, isopropoxy, n-butoxy, isobutoxy, sec-butoxy, tert-butoxy, pentyloxy, 1-methylbutyloxy, 2-methylbutyloxy, 3-methylbutyloxy, 1,2-dimethylpropyloxy, hexyloxy, 1-methylpentyloxy, 1-ethylpropyloxy, 2-methylpentyloxy, 3-methylpentyloxy, 4-methylpentyloxy, 1,2-dimethylbutyloxy, 1,3-dimethylbutyloxy, 2,3-dimethylbutyloxy, 1,1-dimethylbutyloxy, 2,2-dimethylbutyloxy, 3,3-dimethylbutyloxy, and the like. Preferred alkoxy groups include methoxy, ethoxy and propoxy.

Illustrative alkoxycarbonyl groups include, for example, methoxycarbonyl, ethoxycarbonyl, propoxycarbonyl, isopropoxycarbonyl, cyclopropoxycarbonyl, butoxycarbonyl, isobutoxycarbonyl, sec-butoxycarbonyl, tert-butoxycarbonyl, and the like. Preferred alkoxycarbonyl groups include methoxycarbonyl, ethoxycarbonyl, propoxycarbonyl, isopropoxycarbonyl and cyclopropoxycarbonyl.

Illustrative alkyl groups include, for example, methyl, ethyl, n-propyl, isopropyl, n-butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, and the like. Preferred alkyl groups include methyl, ethyl, n-propyl, isopropyl and cyclopropyl.

Illustrative amine groups include, for example, methylamine, dimethylamine, ethylamine, diethylamine, propylamine, dipropylamine, isopropylamine, diisopropylamine, butylamine, dibutylamine, tert-butylamine, di(tert-butyl)amine, ethylmethylamine, butylmethylamine, cyclohexylamine, dicyclohexylamine, and the like. Preferred amine groups include dimethylamine, diethylamine and diisopropylamine.

Illustrative silyl groups include, for example, silyl, trimethylsilyl, triethylsilyl, tris(trimethylsilyl)methyl, trisilylmethyl, methylsilyl and the like. Preferred silyl groups include silyl, trimethylsilyl and triethylsilyl.

Illustrative substituted chleated diene ligands include substituted cyclo-olefins, e.g., cyclopentadiene, the various isomers of cyclohexadiene, cycloheptadiene, cyclooctadiene rings, heterocyclic rings, aromatic rings, and others, as known in the art.

Permissible substituents of the substituted chelated diene ligands include halogen atoms, acyl groups having from 1 to about 12 carbon atoms, alkoxy groups having from 1 to about 12 carbon atoms, alkoxycarbonyl groups having from 1 to about 12 carbon atoms, alkyl groups having from 1 to about 12 carbon atoms, amine groups having from 1 to about 12 carbon atoms or silyl groups having from 0 to about 12 carbon atoms.

In a preferred embodiment, this invention relates in part to organometallic tungsten compounds represented by the following formulae:

Four legged piano stool complexes of tungsten (II)

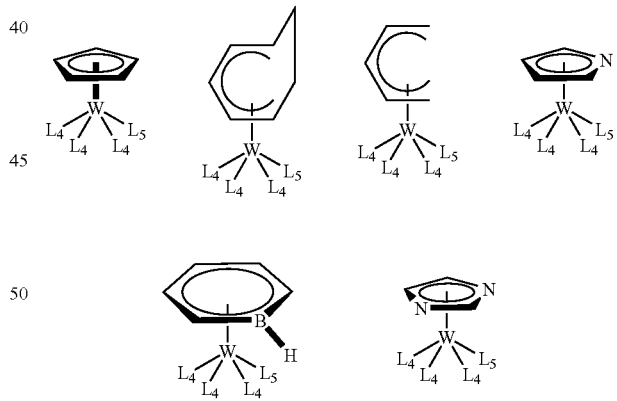

Three legged piano stool complexes of tungsten (0)

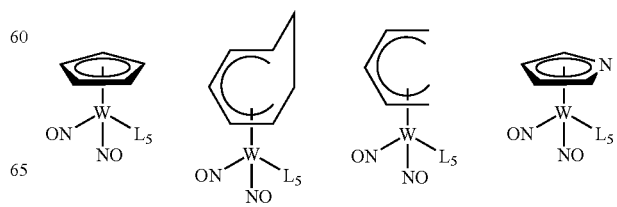

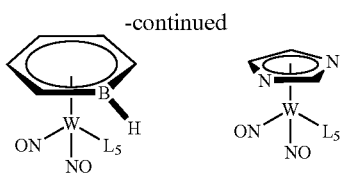

Three legged piano stool complexes of tungsten (II)

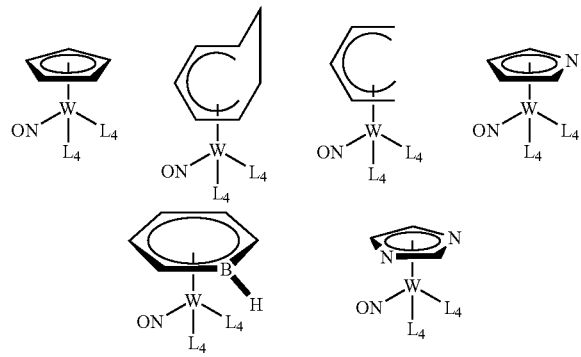

wherein each of $L_4$ and $L_5$ is the same or different and is independently a hydrocarbon group or a heteroatom-containing group.

Illustrative diene derivatives of neutral tungsten complexes can be represented by the formula

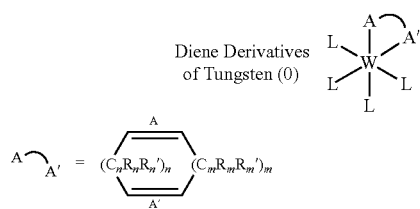

Diene Derivatives of Tungsten (0)

wherein L is a substituted or unsubstituted neutral 2 electron donor ligand such as carbonyl, phosphino, amino, alkenyl, alkynyl, nitrile (e.g., acetonitrile) and isonitrile, m is an integer of from 0 to 2, n is an integer of from 2 to 4, $R_m$, $R_m'$, $R_n$ and $R_n'$ are independently hydrogen or alkyl having from 1 to about 12 carbon atoms, e.g., methyl, ethyl, n-propyl, i-propyl, and the like, provided at least one of $R_m$, $R_m'$, $R_n$, and $R_n'$ is other than hydrogen.

Illustrative organometallic compounds of this invention include, for example, the following (Cp* represents pentamethylcyclopentadienyl):
tris(carbonyl)(methylcyclopentadienyl)hydridotungsten, (MeCp)W(CO)$_3$H;
tris(carbonyl)(ethylcyclopentadienyl)hydridotungsten, (EtCp)W(CO)$_3$H;
tris(carbonyl)(pentamethylcyclopentadienyl)hydridotungsten, Cp*W(CO)$_3$H;
tris(carbonyl)(methylcyclopentadienyl)methyltungsten, (MeCp)W(CO)$_3$CH$_3$;
tris(carbonyl)(ethylcyclopentadienyl)methyltungsten, (EtCp)W(CO)$_3$CH$_3$;
tris(carbonyl)(pentamethylcyclopentadienyl)methyltungsten, CP*W(CO)$_3$CH$_3$;
tris(carbonyl)(methylcyclopentadienyl)ethyltungsten, (MeCp)W(CO)$_3$C$_2$H$_5$;
tris(carbonyl)(ethylcyclopentadienyl)ethyltungsten, (EtCp)W(CO)$_3$C$_2$H$_5$;
tris(carbonyl)(pentamethylcyclopentadienyl)ethyltungsten, Cp*W(CO)$_3$C$_2$H$_5$;
tris(acetonitrile)(methylcyclopentadienyl)hydridotungsten, (MeCp)W(NCCH$_3$)$_3$H;
tris(acetonitrile)(ethylcyclopentadienyl)hydridotungsten, (EtCp)W(NCCH$_3$)$_3$H;
tris(acetonitrile)(pentamethylcyclopentadienyl)hydridotungsten, Cp*W(NCCH$_3$)$_3$H;
tris(carbonyl)(cycloheptadienyl)hydridotungsten, (C$_7$H$_9$)W(CO)$_3$H;
tris(carbonyl)(2,4-dimethylpentadienyl)hydridotungsten, ((CH$_3$)$_2$C$_5$H$_5$)W(CO)$_3$H;
tris(carbonyl)(2,5-dimethylpyrrolyl)hydridotungsten, ((CH$_3$)$_2$C$_4$H$_2$N)W(CO)$_3$H;
methylcyclopentadienylbis(nitrosyl)hydridotungsten, (EtCp)W(NO)$_2$H;
ethylcyclopentadienylbis(nitrosyl)hydridotungsten, (MeCp)W(NO)$_2$H;
pentamethylcyclopentadienylbis(nitrosyl)hydridotungsten, Cp*W(NO)$_2$H;
methylcyclopentadienylbis(nitrosyl)methyltungsten, (EtCp)W(NO)$_2$CH$_3$;
ethylcyclopentadienylbis(nitrosyl)methyltungsten, (MeCp)W(NO)$_2$CH$_3$;
pentamethylcyclopentadienylbis(nitrosyl)methyltungsten, Cp*W(NO)$_2$CH$_3$;
methylcyclopentadienylbis(nitrosyl)ethyltungsten, (EtCp)W(NO)$_2$C$_2$H$_5$;
ethylcyclopentadienylbis(nitrosyl)ethyltungsten, (MeCp)W(NO)$_2$C$_2$H$_5$;
pentamethylcyclopentadienylbis(nitrosyl)ethyltungsten, Cp*W(NO)$_2$C$_2$H$_5$;
cycloheptadienylbis(nitrosyl)hydridotungsten, (C$_7$H$_9$)W(NO)$_2$H;
(2,4-dimethylpentadienyl)bis(nitrosyl)hydridotungsten, ((CH$_3$)$_2$C$_5$H$_5$)W(NO)$_2$H;
(2,5-dimethylpyrrolyl)bis(nitrosyl)hydridotungsten, ((CH$_3$)$_2$C$_4$H$_2$N)W(NO)$_2$H;
methylcyclopentadienylnitrosylbis(hydrido)tungsten, (MeCp)W(NO)H$_2$;
ethylcyclopentadienylnitrosylbis(hydrido)tungsten, (EtCp)W(NO)H$_2$;
pentamethylcyclopentadienylnitrosylbis(hydrido)tungsten, Cp*W(NO)H$_2$;
methylcyclopentadienylnitrosylbis(methyl)tungsten, (MeCp)W(NO)(CH$_3$)$_2$;
ethylcyclopentadienylnitrosylbis(methyl)tungsten, (EtCp)W(NO)(CH$_3$)$_2$;
pentamethylcyclopentadienylnitrosylbis(methyl)tungsten, Cp*W(NO)(CH$_3$)$_2$;
methylcyclopentadienylnitrosylbis(ethyl)tungsten, (MeCp)W(NO)(C$_2$H$_5$)$_2$;
ethylcyclopentadienylnitrosylbis(ethyl)tungsten, (EtCp)W(NO)(C$_2$H$_5$)$_2$;
pentamethylcyclopentadienylnitrosylbis(ethyl)tungsten, Cp*W(NO)(C$_2$H$_5$)$_2$;
cycloheptadienylnitrosylbis(ethyl)tungsten, (C$_7$H$_9$)W(NO)(C$_2$H$_5$)$_2$;
2,4-dimethylpentadienylnitrosylbis(ethyl)tungsten, ((CH$_3$)$_2$C$_5$H$_5$)W(NO)(C$_2$H$_5$)$_2$;
2,5-dimethylpyrrolylnitrosylbis(ethyl)tungsten, ((CH$_3$)$_2$C$_4$H$_2$N)W(NO)(C$_2$H$_5$)$_2$;
and the like.

It is believed that the presence of the anionic donor groups enhance preferred physical properties. It is believed that these substituent groups increase organometallic precursor volatility, decrease the temperature required to dissociate the precursor, and lower the boiling point of the organometallic precursor. An increased volatility of the organometallic precursor compounds ensures a sufficiently high concentration of precursor entrained in vaporized fluid flow to the processing chamber for effective deposition of a layer. The improved volatility will also allow the use of vaporization of the organometallic precursor by sublimation and delivery to a processing chamber without risk of premature dissociation. Additionally, the presence of the 6 electron anionic donor substituent groups may also provide sufficient solubility of the organometallic precursor for use in liquid delivery systems.

It is believed that the organometallic precursors described herein have functional groups which allow the formation of heat decomposable organometallic compounds that are thermally stable at temperatures below about 150° C. and are capable of thermally dissociating at a temperature above about 150° C. The organometallic precursors are also capable of dissociation in a plasma generated by supplying a power density at about 0.6 Watts/cm$^2$ or greater, or at about 200 Watts or greater for a 200 mm substrate, to a processing chamber.

The organometallic precursors described herein may deposit metal and metal carbide layers depending on the processing gas composition and the plasma gas composition for the deposition process. A metal or metal carbide layer is deposited in the presence of inert processing gases such as argon, a reactant processing gas, such as hydrogen, and combinations thereof.

It is believed that the use of a reactant processing gas, such as hydrogen, facilitates reaction with the 6 electron anionic donor groups to form volatile gases, thereby removing the substituents from the precursor and depositing a metal or metal carbide layer on the substrate. The metal layer is preferably deposited in the presence of argon.

An exemplary processing regime for depositing a layer from the above described precursor is as follows. A precursor having the composition described herein, such as tris(carbonyl)(methylcyclopentadienyl)hydridotungsten and a processing gas is introduced into a processing chamber. The precursor is introduced at a flow rate between about 5 and about 500 sccm and the processing gas is introduced into the chamber at a flow rate of between about 5 and about 500 sccm. In one embodiment of the deposition process, the precursor and processing gas are introduced at a molar ratio of about 1:1. The processing chamber is maintained at a pressure between about 100 milliTorr and about 20 Torr. The processing chamber is preferably maintained at a pressure between about 100 milliTorr and about 250 milliTorr. Flow rates and pressure conditions may vary for different makes, sizes, and models of the processing chambers used.

Thermal dissociation of the precursor involves heating the substrate to a temperature sufficiently high to cause the hydrocarbon portion of the volatile metal compound adjacent the substrate to dissociate to volatile hydrocarbons which desorb from the substrate while leaving the metal on the substrate. The exact temperature will depend upon the identity and chemical, thermal, and stability characteristics of the organometallic precursor and processing gases used under the deposition conditions. However, a temperature from about room temperature to about 400° C. is contemplated for the thermal dissociation of the precursor described herein.

The thermal dissociation is preferably performed by heating the substrate to a temperature between about 100° C. and about 400° C. In one embodiment of the thermal dissociation process, the substrate temperature is maintained between about 250° C. and about 450° C. to ensure a complete reaction between the precursor and the reacting gas on the substrate surface. In another embodiment, the substrate is maintained at a temperature below about 400° C. during the thermal dissociation process.

For plasma-enhanced CVD processes, power to generate a plasma is then either capacitively or inductively coupled into the chamber to enhance dissociation of the precursor and increase reaction with any reactant gases present to deposit a layer on the substrate. A power density between about 0.6 Watts/cm$^2$ and about 3.2 Watts/cm$^2$, or between about 200 and about 1000 Watts, with about 750 Watts most preferably used for a 200 mm substrate, is supplied to the chamber to generate the plasma.

After dissociation of the precursor and deposition of the material on the substrate, the deposited material may be exposed to a plasma treatment. The plasma comprises a reactant processing gas, such as hydrogen, an inert gas, such as argon, and combinations thereof. In the plasma-treatment process, power to generate a plasma is either capacitively or inductively coupled into the chamber to excite the processing gas into a plasma state to produce plasma specie, such as ions, which may react with the deposited material. The plasma is generated by supplying a power density between about 0.6 Watts/cm$^2$ and about 3.2 Watts/cm$^2$, between about 200 and about 1000 Watts for a 200 mm substrate, to the processing chamber.

In one embodiment the plasma treatment comprises introducing a gas at a rate between about 5 sccm and about 300 sccm into a processing chamber and generating a plasma by providing power density between about 0.6 Watts/cm$^2$ and about 3.2 Watts/cm$^2$, or a power at between about 200 Watts and about 1000 Watts for a 200 mm substrate, maintaining the chamber pressure between about 50 milliTorr and about 20 Torr, and maintaining the substrate at a temperature of between about 100° C. and about 400° C. during the plasma process.

It is believed that the plasma treatment lowers the layer's resistivity, removes contaminants, such as carbon or excess hydrogen, and densifies the layer to enhance barrier and liner properties. It is believed that species from reactant gases, such as hydrogen species in the plasma react with the carbon impurities to produce volatile hydrocarbons that can easily desorb from the substrate surface and can be purged from the processing zone and processing chamber. Plasma species from inert gases, such as argon, further bombard the layer to remove resistive constituents to lower the layers resistivity and improve electrical conductivity.

Plasma treatments are preferably not performed for metal carbide layers, since the plasma treatment may remove the desired carbon content of the layer. If a plasma treatment for a metal carbide layer is performed, the plasma gases preferably comprise inert gases, such as argon and helium, to remove carbon.

It is believed that depositing layers from the above identified precursors and exposing the layers to a post deposition plasma process will produce a layer with improved material properties. The deposition and/or treatment of the materials described herein are believed to have improved diffusion resistance, improved interlayer adhesion, improved thermal stability, and improved interlayer bonding.

In an embodiment of this invention, a method for metallization of a feature on a substrate is provided that comprises depositing a dielectric layer on the substrate, etching a pattern into the substrate, depositing a metal carbide layer on the dielectric layer, and depositing a conductive metal layer on the metal carbide layer. The substrate may be optionally exposed to reactive pre-clean comprising a plasma of hydrogen and argon to remove oxide formations on the substrate prior to deposition of the metal carbide layer. The conductive metal is preferably copper and may be deposited by physical vapor deposition, chemical vapor deposition, or electrochemical deposition. The metal layer and the metal carbide layer are deposited by the thermal or plasma enhanced dissociation of an organometallic precursor of this invention in the presence of a processing gas, preferably at a pressure less than about 20 Torr. Once deposited, the metal layer and the metal carbide layer can be exposed to a plasma prior to subsequent layer deposition.

Current copper integration schemes involve a diffusion barrier with a copper wetting layer on top followed by a copper seed layer. A layer of tungsten carbide gradually becoming tungsten rich in accordance with this invention would replace multiple steps in the current integration schemes. The tungsten carbide layer is an excellent barrier to copper diffusion due to its amorphous character. The tungsten rich layer functions as a wetting layer and may allow for direct plating onto the tungsten. This single layer could be deposited in one step by manipulating the deposition parameters during the deposition. A post deposition treatment may also be employed to increase the ratio of tungsten in the film. Removal of one or more steps in semiconductor manufacture will result in substantial savings to the semiconductor manufacturer.

Tungsten carbide films are deposited at temperatures lower than 400° C. and form no corrosive byproducts. Tungsten carbide films are amorphous and are superior barriers than WN to copper diffusion. By tuning the deposition parameters and post deposition treatment, the tungsten carbide barrier can have a tungsten rich film deposited on top of it. This tungsten rich film acts as a wetting layer for copper and may allow for direct copper plating on top of the tungsten layer. In an embodiment, the deposition parameters may be tuned to provide a layer in which the composition varies across the thickness of the layer. For example, the layer may be tungsten carbide rich at the silicon portion surface of the microchip, e.g., good barrier properties, and tungsten rich at the copper layer surface, e.g., good adhesive properties.

As also indicated above, this invention also relates in part to a process for producing the organometallic compound represented by the formulae above, for example, an organometallic compound having the formula $(L_1)_y M(L_2)_{z-y}$, wherein M is a Group 5 metal or a Group 6 metal, $L_1$ is a substituted or unsubstituted anionic 6 electron donor ligand, $L_2$ is the same or different and is (i) a substituted or unsubstituted anionic 2 electron donor ligand, (ii) a substituted or unsubstituted cationic 2 electron donor ligand, or (iii) a substituted or unsubstituted neutral 2 electron donor ligand; $y$ is an integer of 1, and $z$ is the valence of M; and wherein the sum of the oxidation number of M and the electric charges of $L_1$ and $L_2$ is equal to 0, which process comprises reacting a metal halide, a salt and a reducing agent in the presence of a first solvent and under reaction conditions sufficient to produce an intermediate reaction material, and reacting said intermediate reaction material with a base material in the presence of a second solvent and under reaction conditions sufficient to produce said organometallic compound. The organometallic compound yield resulting from the process of this invention can be 40% or greater, preferably 35% or greater, and more preferably 30% or greater.

The process is particularly well-suited for large scale production since it can be conducted using the same equipment, some of the same reagents and process parameters that can easily be adapted to manufacture a wide range of products. The process provides for the synthesis of organometallic precursor compounds using a process where all manipulations can be carried out in a single vessel, and which route to the organometallic precursor compounds does not require the isolation of an intermediate complex.

The metal halide compound starting material may be selected from a wide variety of compounds known in the art. The invention herein most prefers metals selected from tungsten (W), tantalum (Ta), molybdenum (Mo), niobium (Nb), vanadium (V) or chromium (Cr). Illustrative metal halide compounds include, for example, tungsten hexachloride, molybdenum hexachloride, chromium hexachloride, tantalum pentachloride, niobium pentachloride or vanadium pentachloride, and the like.

The concentration of the metal source compound starting material can vary over a wide range, and need only be that minimum amount necessary to react with the salt and reducing agent to produce the intermediate reaction material and to provide the given metal concentration desired to be employed and which will furnish the basis for at least the amount of metal necessary for the organometallic compounds of this invention. In general, depending on the size of the reaction mixture, metal source compound starting material concentrations in the range of from about 1 millimole or less to about 10,000 millimoles or greater, should be sufficient for most processes.

The salt starting material may be selected from a wide variety of compounds known in the art. Illustrative salts include sodium cyclopentadiene, potassium cyclopentadiene, lithium cyclopentadiene or magnesocene, and the like. The salt starting material is preferably sodium cyclopentadiene and the like.

The concentration of the salt starting material can vary over a wide range, and need only be that minimum amount necessary to react with the metal source compound starting material and reducing agent to produce an intermediate reaction material. In general, depending on the size of the first reaction mixture, salt starting material concentrations in the range of from about 1 millimole or less to about 10,000 millimoles or greater, should be sufficient for most processes.

The reducing agent starting material may be selected from a wide variety of materials known in the art. Illustrative reducing agents include sodium bis(2-methoxyethoxy)aluminum dihydride (e.g., Red-Al® and Vitride reducing agent materials), sodium borohydride, lithium aluminum hydride, and the like. The reducing agent material is preferably sodium bis(2-methoxyethoxy)aluminum dihydride (e.g., Red-Al® reducing agent material), and the like.

The concentration of the reducing agent starting material can vary over a wide range, and need only be that minimum amount necessary to react with the metal source compound starting material and salt starting material to produce an intermediate reaction material. In general, depending on the size of the first reaction mixture, reducing agent starting material concentrations in the range of from about 1 millimole or less to about 10,000 millimoles or greater, should be sufficient for most processes.

The first solvent employed in the method of this invention may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, silicone oils, other aprotic solvents, or mixtures of one or more of the above; more preferably, diethylether, pentanes, or dimethoxyethanes; and most preferably toluene or dimethoxyethane (DME) or mixtures thereof. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the reaction of the salt compound and reducing agent with the metal source compound to produce the intermediate reaction material, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 120° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

The intermediate reaction material may be selected from a wide variety of materials known in the art. Illustrative intermediate reaction materials include salts of anionic Group 6 metals with one negatively charged 6-electron donor and 3 neutral 2-electron donors such as $Li[(EtCp)W(CO)_3]$, $Na[(EtCp)W(CO)_3]$, $PPN[(2,5-dimethylpyrrolyl)W(CO)_3]$, and the like. The intermediate reaction material is preferably $Li[(EtCp)W(CO)_3]$. The process of this invention does not require isolation of the intermediate reaction material.

The concentration of the intermediate reaction material can vary over a wide range, and need only be that minimum amount necessary to react with the base material to produce the organometallic compounds of this invention. In general, depending on the size of the second reaction mixture, intermediate reaction material concentrations in the range of from about 1 millimole or less to about 10,000 millimoles or greater, should be sufficient for most processes.

The base material may be selected from a wide variety of materials known in the art. Illustrative base materials include sodium hydroxide, potassium hydroxide, ethyl acetate, and the like. The base material is preferably sodium hydroxide and the like.

The concentration of the base material can vary over a wide range, and need only be that minimum amount necessary to react with the intermediate reaction material to produce the organometallic compounds of this invention. In general, depending on the size of the second reaction mixture, base material concentrations in the range of from about 1 millimole or less to about 10,000 millimoles or greater, should be sufficient for most processes.

The second solvent employed in the method of this invention may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, silicone oils, other aprotic solvents, or mixtures of one or more of the above; more preferably, diethylether, pentanes, or dimethoxyethanes; and most preferably toluene, hexane or mixtures thereof. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the reaction of the intermediate reaction material with the base material to produce the organometallic precursors of this invention, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 120° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

In an embodiment, the 4 legged piano stool complexes of tungsten(II) depicted above can be prepared by the following synthetic method:

1) the reaction of a salt or complex of a negatively charged 6-electron donor (e.g., $L_1(EtCp)$ or $Bu_3Sn(EtCp)$), with a tungsten (0) complex with 6 neutral 2-electron donors (e.g., $W(CO)_6$) to yield a tungstenate anion salt in which 3 neutral 2-electron donor ligands, and 1 negatively charged 6-electron donor ligand are directly coordinated to the tungsten;

2) the reaction of a second component, e.g., acetic acid or trimethyl bromine, with the intermediate tungstenate anion salt to afford a tungsten (II) complex with 1 negatively charged 6-electron donor ligand, 3 neutral 2-electron donor ligands and 1 negatively charged 2-electron donor ligand.

Isolation of the complex may be achieved by filtering to remove solids, reduced pressure to remove solvent, and distillation (or sublimation) to afford the final pure compound. Chromatography may also be employed as a final purification method.

One example of reaction 1 above (reaction scheme 1 below) and two examples of reaction 2 above (reaction schemes 2a and 2b below) are shown below:

Equation 1

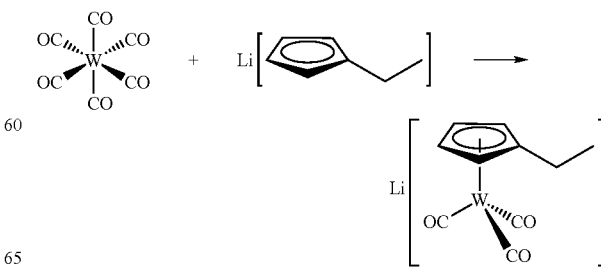

Equation 2a

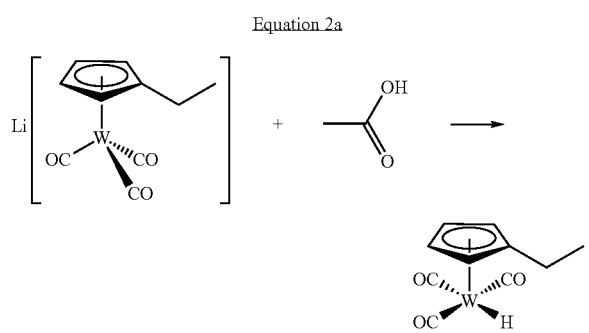

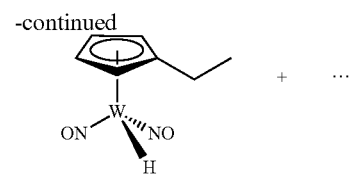

Equation 2b

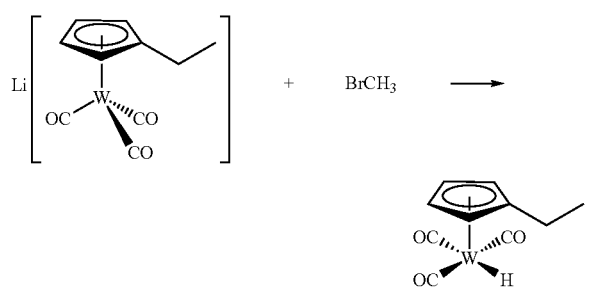

In an embodiment, the 3 legged piano stool complexes of tungsten (0) depicted above may similarly be prepared by the following synthetic method:

1) $[W(NO)_2X_2]_n$ where X is a halide is reacted with a salt or complex of the negatively charged 6-electron donor (e.g., $Bu_3Sn(EtCp)$) to afford an intermediate complex with one halide ligand, 2 nitrosyl ligands and a negatively charged 6-electron donor ligand;

2) the halide complex (e.g., $(EtCp)W(NO)_2Cl$) may be reacted with a second source, e.g., $Na[AlH_2(OCH_2CH_2OMe)_2]$, to afford a halide salt and a neutral tungsten (0) organometallic compound. Examples of the second source include, methyllithium, $Na[AlH_2(OCH_2CH_2OMe)_2]$, and the like. This synthetic method is shown below.

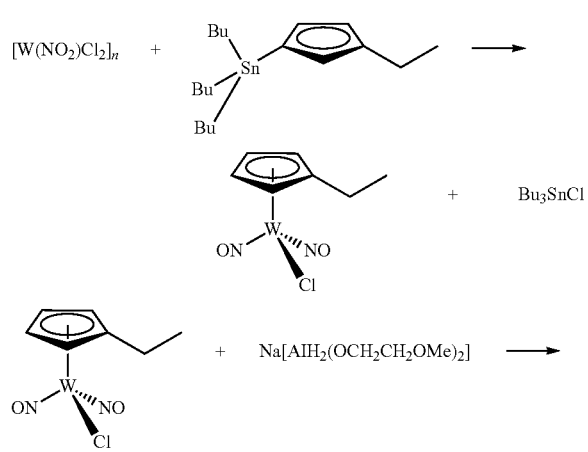

The use of a diene with a pendant alkyl chain can reduce the melting point of an organometallic precursor complex by introducing additional entropy. The methods of synthesis of diene derivatives of tungsten (0) typically involve either photochemical or thermally catalyzed substitution of $W(CO)_6$ by the diene complex. Examples of dienes that may be expected to assist in melting point reduction are 2-ethylcycloocta-1,4-diene and 3-ethylcycloocta-1,4-diene.

Illustrative synthetic methods in which an alkyl substituted diene could be substituted for the diene reported to obtain the organometallic compound having a substituted chelated diene ligand herein include: 1) Fischer, E. O. et. al., *Chem. Ber.*, 1959, 92, 2995; 2) Leigh, G. J., et. al., *J. Organomet. Chem.*, 1965, 4, 461; and 3) Laine, R. M., *Transition Met. Chem.*, 1990, 5, 158.

Other alternative processes that may be used in preparing the organometallic compounds of this invention include those disclosed in U.S. Pat. No. 6,605,735 B2 and U.S. Patent Application Publication No. US 2004/0127732 A1, published Jul. 1, 2004, the disclosure of which is incorporated herein by reference. The organometallic compounds of this invention may also be prepared by conventional processes such as described in Legzdins, P. et al. Inorg. Synth. 1990, 28, 196 and references therein.

For organometallic compounds prepared by the method of this invention, purification can occur through recrystallization, more preferably through extraction of reaction residue (e.g., hexane) and chromatography, and most preferably through sublimation and distillation.

Those skilled in the art will recognize that numerous changes may be made to the method described in detail herein, without departing in scope or spirit from the present invention as more particularly defined in the claims below.

Examples of techniques that can be employed to characterize the organometallic compounds formed by the synthetic methods described above include, but are not limited to, analytical gas chromatography, nuclear magnetic resonance, thermogravimetric analysis, inductively coupled plasma mass spectrometry, differential scanning calorimetry, vapor pressure and viscosity measurements.

Relative vapor pressures, or relative volatility, of organometallic compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

The organometallic compound precursors described herein are well suited for preparing in-situ powders and coatings. For instance, an organometallic compound precursor can be applied to a substrate and then heated to a temperature sufficient to decompose the precursor, thereby forming a metal or metal carbide/nitride, e.g., tungsten, tungsten nitride, tungsten carbide, or tungsten carbonitride, coating on the substrate. Applying the precursor to the substrate can be by painting, spraying, dipping or by other techniques known in the art. Heating can be conducted in an oven, with a heat gun, by electrically heating the substrate, or by other means, as known in the art. A layered coating can be obtained by applying an organometallic compound precursor, and heating and decomposing it, thereby forming a first layer, followed by at least one other coating with the same or different precursors, and heating.

Organometallic compound precursors such as described above also can be atomized and sprayed onto a substrate. Atomization and spraying means, such as nozzles, nebulizers and others, that can be employed are known in the art.

This invention provides in part an organometallic precursor and a method of forming a metal or metal carbide layer on a substrate by CVD or ALD of the organometallic precursor. In one aspect of the invention, an organometallic precursor of this invention is used to deposit a metal or metal carbide layer at subatmospheric pressures. The method for depositing the metal or metal carbide layer comprises introducing the precursor into a processing chamber, preferably maintained at a pressure of less than about 20 Torr, and dissociating the precursor in the presence of a processing gas to deposit a metal or metal carbide layer. The precursor may be dissociated and deposited by a thermal or plasma-enhanced process. The method may further comprise a step of exposing the deposited layer to a plasma process to remove contaminants, densify the layer, and reduce the layer's resistivity.

In preferred embodiments of the invention, an organometallic compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic compound precursor, such as described above, also can be employed in a given process.

As indicated above, this invention also relates in part to a method for producing a film, coating or powder. The method includes the step of decomposing at least one organometallic compound precursor, thereby producing the film, coating or powder, as further described below.

Deposition methods described herein can be conducted to form a film, powder or coating that includes a single metal or a film, powder or coating that includes a single metal or metal carbide/nitride, e.g., tungsten, tungsten nitride, tungsten carbide, or tungsten carbonitride. Mixed films, powders or coatings also can be deposited, for instance mixed metal/metal carbide films.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of this invention, for instance, can be considered for fabricating metal electrodes, in particular as n-channel metal electrodes in logic, as capacitor electrodes for DRAM applications, and as dielectric materials.

The method also is suited for preparing layered films, wherein at least two of the layers differ in phase or composition. Examples of layered film include metal-insulator-semiconductor, and metal-insulator-metal.

In an embodiment, the invention is directed to a method that includes the step of decomposing vapor of an organometallic compound precursor described above, thermally, chemically, photochemically or by plasma activation, thereby forming a film on a substrate. For instance, vapor generated by the compound is contacted with a substrate having a temperature sufficient to cause the organometallic compound to decompose and form a film on the substrate.

The organometallic compound precursors can be employed in chemical vapor deposition or, more specifically, in metal organic chemical vapor deposition processes known in the art. For instance, the organometallic compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organometallic compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The method of the invention can be conducted in various chemical vapor deposition reactors, such as, for instance, hot or cold-wall reactors, plasma-assisted, beam-assisted or laser-assisted reactors, as known in the art.

Examples of substrates that can be coated employing the method of the invention include solid substrates such as metal substrates, e.g., Al, Ni, Ti, Co, Pt, metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The method of this invention can be conducted to deposit a film on a substrate that has a smooth, flat surface. In an embodiment, the method is conducted to deposit a film on a substrate used in wafer manufacturing or processing. For instance, the method can be conducted to deposit a film on patterned substrates that include features such as trenches, holes or vias. Furthermore, the method of the invention also can be integrated with other steps in wafer manufacturing or processing, e.g., masking, etching and others.

In an embodiment of this invention, a plasma assisted ALD (PEALD) method has been developed for using the organometallic precursors to deposit tungsten carbide and tungsten rich films. The solid precursor can be sublimed under the flow of an inert gas to introduce it into a CVD chamber. Tungsten carbide films are grown on a substrate with the aid of a hydrogen plasma. The ratio of tungsten to carbon can be controlled by controlling the pulse duration of the hydrogen plasma.

Chemical vapor deposition films can be deposited to a desired thickness. For example, films formed can be less than 1 micron thick, preferably less than 500 nanometers and more preferably less than 200 nanometers thick. Films that are less than 50 nanometers thick, for instance, films that have a thickness between about 0.1 and about 20 nanometers, also can be produced.

Organometallic compound precursors described above also can be employed in the method of the invention to form films by ALD processes or atomic layer nucleation (ALN) techniques, during which a substrate is exposed to alternate pulses of precursor, oxidizer and inert gas streams. Sequential layer deposition techniques are described, for example, in U.S. Pat. No. 6,287,965 and in U.S. Pat. No. 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. milliseconds) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

This invention includes a method for forming a metal material, e.g., tungsten, tungsten nitride, tungsten carbide, or tungsten carbonitride, on a substrate, e.g., a microelectronic device structure, from an organometallic precursor of this invention, said method comprising vaporizing said organometallic precursor to form a vapor, and contacting the vapor with the substrate to form said metal material thereon. After tungsten, tungsten nitride, tungsten carbide, or tungsten carbonitride is deposited on the substrate, the substrate may thereafter be metallized with copper or integrated with a ferroelectric thin film.

The method of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organometallic compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate.

In an example, the deposition process is conducted in a reaction chamber that houses one or more substrates. The substrates are heated to the desired temperature by heating the entire chamber, for instance, by means of a furnace. Vapor of the organometallic compound can be produced, for example, by applying a vacuum to the chamber. For low boiling compounds, the chamber can be hot enough to cause vaporization of the compound. As the vapor contacts the heated substrate surface, it decomposes and forms a metal or metal carbide film. As described above, an organometallic compound precursor can be used alone or in combination with one or more components, such as, for example, other organometallic precursors, inert carrier gases or reactive gases.

In a system that can be used in producing films by the method of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organometallic compound precursors described above can be employed to produce films that include a single metal or a film that includes a single metal carbide. Mixed films also can be deposited, for instance mixed metal carbide films. Such films are produced, for example, by employing several organometallic precursors. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

In addition to their use in semiconductor applications as chemical vapor or atomic layer deposition precursors for film depositions, the organometallic compounds of this invention may also be useful, for example, as catalysts, fuel additives and in organic syntheses.

Various modifications and variations of this invention will be obvious to a worker skilled in the art and it is to be understood that such modifications and variations are to be included within the purview of this application and the spirit and scope of the claims.

EXAMPLE 1

Synthesis of Lithium Ethylcyclopentadienide

An oven dried 2.0 liter round-bottomed 3 necked flask was equipped with a Teflon coated stir bar, and a 500 milliliter dropping funnel, and a stopcock adapter. The remaining neck on the flask was sealed with a rubber septum. The flask was then connected to a nitrogen/vacuum manifold via Tygon® tubing, and the contents of the flask were evacuated and backfilled with nitrogen three times.

Anhydrous hexanes (500 milliliter) was then cannulated into the flask and the 2.0 liter flask was cooled inside of a cooling bath to −10° C. To this solution, freshly cracked ethylcyclopentadiene (97.5 grams, 1.06 mol) was added. N-butyllithium (380 milliliters, 2.5 M in hexanes, 1.0 mol) was then added to the dropping funnel. The n-butyllithium solution was then added dropwise to the ethycyclopentadiene solution while stirring. The temperature of the reaction was monitored by thermocouple and during the 3 hour addition the temperature was maintained between −10° C. and 0° C. During the addition evidence of an insoluble white precipitate (lithium ethylcyclopentadienide) became apparent.

Once the addition was completed the experimental apparatus was transferred to inside of an inert atmosphere glovebox. The contents of the reaction flask were filtered through a coarse frit and the white solid was rinsed three times with 100 milliliters of hexanes. The fluffy white solid was then dried under vacuum yielding 100.1 grams of lithium ethylcyclopentadienide.

EXAMPLE 2

Synthesis of Li[(EtCp)W(CO)$_3$)]

An oven dried 3.0 liter flask was fitted with a condenser, a mechanical stirring shaft and a rubber septum. A stopcock adapter was fitted to the condenser the assembly was then connected via the stopcock adapter to a nitrogen/vacuum manifold with Tygon® tubing. The contents of the flask were evacuated and backfilled with nitrogen three times.

While under vacuum, the apparatus was disconnected from the nitrogen/vacuum manifold and transferred inside of an inert atmosphere glovebox. The rubber septum was removed and tungsten hexacarbonyl (300 grams, 0.85 mol) was loaded into the 3.0 liter flask. The rubber septum was replaced, the flask was taken out of the glovebox and reconnected to the vacuum/nitrogen manifold.

Dimethoxyethane (1.0 liter, anhydrous) was then cannulated from a Sureseal® bottle into the reaction vessel, and the solution was stirred. The tungsten hexacarbonyl exhibited negligible solubility in this solution, and appeared as a disperse white suspension in the heterogeneous solution.

To a one necked 2.0 liter round-bottomed flask, inside of an inert atmosphere glovebox, lithium ethylcyclopentadienide (85.3 grams) and a Teflon® coated stir bar were added. The neck was sealed with a rubber septum and removed from the glovebox. Dimethoxyethane (500 milliliters, anhydrous) was then canulated into the one neck flasked under an inert nitrogen pad while stirring. The lithium ethylcyclopentadienide fully dissolved in the dimethoxyethane yielding a pale yellow solution.

The lithium ethylcyclopentadienide solution was then cannulated into the flask containing dimethoxyane and W(CO)$_6$ while stirring both reaction flasks. Once the addition was completed, a water flow was initiated through the condenser and the contents of the reaction vessel were heated to reflux. Over the course of the first day the color of the solution went from a pale yellow solution with a white suspension, to a murky red. Initially, mechanical stirring is required to generate sufficient torque for stirring the contents of the reaction vessel, however, at the end of the first day, a Teflon® coated stir bar replaced the mechanical stirring apparatus. At this point, a sufficient portion of the solids have gone into solution such that a Teflon® stir bar is capable of maintaining stirring in the solution.

A gentle reflux was continued for 3 days, prior to cooling the solution to room temperature. At this point the red solution of Li[(EtCp)W(CO)$_3$] may either be used as a synthetic reagent for subsequent syntheses or it may be isolated. Isolation of the salt may be accomplished by removal of solvent under reduced pressure, or the addition of a nonpolar solvent such as pentane. Most frequently, the solution was used as a synthetic intermediate without isolation in the preparation of volatile W based organometallics.

EXAMPLE 3

Synthesis of (EtCp)W(CO)$_3$H

To a 3 necked 1.0 liter flask, a stirring bar and 2 rubber septa and a stopcock adapter were connected. The flask was then connected to a nitrogen/vacuum manifold and evacuated and refilled three times. Dimethoxyethane (500 milliliters) was then cannulated into the vessel and the liquid was stirred. Glacial acetic acid (51 grams, 0.85 mol) was then added to the vessel by syringe through a rubber septa. The solution was then sparged with N$_2$ for 30 minutes.

A solution of Li[(EtCp)W(CO)$_3$] in dimethoxyethane (0.85 mol Li[(EtCp)W(CO)$_3$] in 1.5 liters of DME)] was prepared as described in Example 2. A rubber septum was removed and replaced with an oven dried inert atmosphere 1.0 liter dropping funnel.

The glacial acetic acid solution in DME was then transferred from the 1.0 liter flask to the 1.0 liter dropping funnel by canula under an inert N$_2$ pad. The contents of the dropping funnel were added dropwise over 2 hours. During this time brown solids precipitated from the red solution. Following the addition, the contents of the reaction flask were permitted to stir overnight.

The 3.0 liter flask was then transferred inside of an inert atmosphere glovevox and the contents of the reaction vessel were filtered through a coarse frit into a 3.0 liter two necked round-bottomed flask. The solid collected on the frit was discarded. Once the filtered solution was transferred, the flask was fit with an inert atmosphere distillation head and removed from the glovebox under a nitrogen pad.

The distillation was initially conducted at atmospheric pressure to remove the dimethoxyethane. Once the majority of the dimethoxyane had been removed, the distillation was conducted at reduced pressure. Multiple cuts were collected and there was evidence of W(CO)$_6$ sublimation early during the distillation. 248 grams of the desired product yellow liquid product (EtCp)W(CO)$_3$H was collected at a pressure of $3 \times 10^{-1}$ Torr and at a head temperature of 81° C. (EtCp)W(CO)$_3$H was characterized by $^1$H NMR, TGA, GC and DSC.

EXAMPLE 4

Synthesis of (EtCp)W(CO)CH$_3$

To a 3 necked 1.0 liter flask, a stirring bar and 2 rubber septa and a stopcock adapter were connected. The flask was then connected to a nitrogen/vacuum manifold and evacuated and refilled three times. Dimethoxyethane (500 milliliters) was then cannulated into the vessel and the liquid was stirred. Bromomethane (81 grams, 0.85 mol) was then added to the vessel by syringe through a rubber septa. The solution was then sparged with N$_2$ for 30 minutes.

A solution of Li[(EtCp)W(CO)$_3$] in dimethoxyethane (0.85 mol Li[(EtCp)W(CO)$_3$] in 1.5 liters of DME)] was prepared as described in Example 2. A rubber septum was removed and replaced with an oven dried inert atmosphere 1.0 liter dropping funnel.

The bromomethane solution in DME was then transferred from the 1.0 liter flask to the 1.0 liter dropping funnel by canula under an inert $N_2$ pad. The contents of the dropping funnel were added dropwise over 2 hours. During this time brown solids precipitated from the red solution. Following the addition, the contents of the reaction flask were permitted to stir overnight.

The 3.0 liter flask was then transferred inside of an inert atmosphere glove box and the contents of the reaction vessel were filtered through a coarse frit into a 3.0 liter two necked round-bottomed flask. The solid collected on the frit was discarded. Once the filtered solution was transferred, the flask was fit with an inert atmosphere distillation head and removed from the glovebox under a nitrogen pad.

The distillation was initially conducted at atmospheric pressure to remove the dimethoxyethane. Once the majority of the dimethoxyane had been removed, the distillation was conducted at reduced pressure. Multiple cuts were collected and there was evidence of $W(CO)_6$ sublimation early during the distillation. 227 grams of the desired product yellow liquid product $(EtCp)W(CO)_3CH_3$ was collected at a pressure of $3\times10^{-1}$ Torr and at a head temperature of 94° C.

The invention claimed is:

1. A compound having the formula $(L_1)_y M(L_2)_{z-y}$ wherein M is a Group 5 metal selected from tantalum (Ta), niobium (Nb) or vanadium (V), or a Group 6 metal selected from tungsten (W) or chromium (Cr), $L_1$ is a substituted anionic 6 electron donor ligand, $L_2$ is the same or different and is (i) a substituted or unsubstituted anionic 2 electron donor ligand, and at least one of (ii) a substituted or unsubstituted cationic 2 electron donor ligand, and (iii) a substituted or unsubstituted neutral 2 electron donor ligand; y is an integer of 1, and z is the valence of M; and wherein the sum of the oxidation number of M and the electric charges of $L_1$ and $L_2$ is equal to 0.

2. The compound of claim 1 wherein M is selected from tungsten (W), tantalum (Ta), niobium (Nb), vanadium (V) or chromium (Cr), $L_1$ is a substituted anionic 6 electron donor ligand selected from cyclopentadienyl, cycloheptadienyl, pentadienyl, pyrrolyl, imidazolyl, pyrazolyl and boratabenzyl, and $L_2$ is (i) a substituted or unsubstituted anionic 2 electron donor ligand selected from hydrido, halo and an alkyl group having from 1 to 12 carbon atoms, and at least one of (ii) a substituted or unsubstituted cationic 2 electron donor ligand selected from nitrosyls, and (iii) a substituted or unsubstituted neutral 2 electron donor ligand selected from carbonyl, phosphino, amino, alkenyl, alkynyl, nitrile and isonitrile.

3. The compound of claim 1 selected from the following: (i) M is tungsten (W) with a (+2) oxidation number, $L_1$ is a substituted anionic 6 electron donor ligand with a (−1) electrical charge, one $L_2$ ligand is a substituted or unsubstituted anionic 2 electron donor ligand with a (−1) electrical charge, and the remaining three $L_2$ ligands are the same or different and are each a substituted or unsubstituted neutral 2 electron donor ligand with a zero (0) electrical charge; and (ii) M is tungsten (W) with a (0) oxidation number, $L_1$ is a substituted anionic 6 electron donor ligand with a (−1) electrical charge, one $L_2$ ligand is a substituted or unsubstituted anionic 2 electron donor ligand with a (−1) electrical charge, and the remaining two $L_2$ ligands are the same or different and are each a substituted or unsubstituted cationic 2 electron donor ligand with a (+1) electrical charge.

4. The compound of claim 1 selected from:
(i) a compound having the formula $L_1 M''(L_3)_x(L_4)_y(L_5)_{z'}$ wherein M'' is a Group 6 metal selected from tungsten (W) or chromium (Cr) having an oxidation state of n, $L_1$ is a substituted anionic 6 electron donor ligand, $L_3$ is the same or different and is a substituted or unsubstituted cationic 2 electron donor ligand, $L_4$ is the same or different and is a substituted or unsubstituted neutral 2 electron donor ligand, $L_5$ is the same or different and is a substituted or unsubstituted anionic 2 electron donor ligand; n is an integer of 0 or 2, z' is an integer of 0 or 1, x is an integer equal to z'−n+1 provided that x is greater than or equal to 0, and y is an integer equal to 7n/2+2x−4z' provided that y' is greater than or equal to 0; and wherein the sum of the oxidation number of M'' and the electric charges of $L_1$, $L_3$, $L_4$ and $L_5$ is equal to 0;
(ii) a compound having the formula $(L_1)_y M(CO)_x (L_6)_{z-y-x'}$ wherein M is a Group 5 metal selected from tantalum (Ta), niobium (Nb) or vanadium (V), or a Group 6 metal selected from tungsten (W) or chromium (Cr), $L_1$ is a substituted anionic 6 electron donor ligand, $L_6$ is the same or different and is (i) a substituted or unsubstituted anionic 2 electron donor ligand, and optionally (ii) a substituted or unsubstituted cationic 2 electron donor ligand; x' is an integer of from 0 to 3, y is an integer of 1, and z is the valence of M; and wherein the sum of the oxidation number of M and the electric charges of $L_1$, $L_6$ and CO groups is equal to 0;
(iii) a compound having the formula $L_1 M'L_4(L_5)_3$ wherein M' is a Group 5 metal selected from tantalum (Ta), niobium (Nb) or vanadium (V), $L_1$ is a substituted anionic 6 electron donor ligand, $L_4$ is a substituted or unsubstituted neutral 2 electron donor ligand, and $L_5$ is the same or different and is a substituted or unsubstituted anionic 2 electron donor ligand; and wherein the sum of the oxidation number of M' and the electric charges of $L_1$, $L_4$ and $L_5$ is equal to 0;
(iv) a compound having the formula $(L_1)_y M(NO)_{x''} (L_7)_{z-y-x''}$ wherein M is a Group 5 metal selected from tantalum (Ta), niobium (Nb) or vanadium (V), or a Group 6 metal selected from tungsten (W) or chromium (Cr), $L_1$ is a substituted anionic 6 electron donor ligand, $L_7$ is the same or different and is (i) a substituted or unsubstituted anionic 2 electron donor ligand, and optionally (ii) a substituted or unsubstituted neutral 2 electron donor ligand; x'' is an integer of from 0 to 2, y is an integer of 1, and z is the valence of M; and wherein the sum of the oxidation number of M and the electric charges of $L_1$, $L_7$ and NO groups is equal to 0; and
(v) a compound having the formula $L_1 M'(L_3)_2 L_5$ wherein M' is a Group 5 metal selected from tantalum (Ta), niobium (Nb) or vanadium (V), $L_1$ is a substituted anionic 6 electron donor ligand, $L_3$ is the same or different and is a substituted or unsubstituted cationic 2 electron donor ligand, and $L_5$ is a substituted or unsubstituted anionic 2 electron donor ligand; and wherein the sum of the oxidation number of M' and the electric charges of $L_1$, $L_3$ and $L_5$ is equal to 0.

5. The compound of claim 4 selected from:
(i) a compound having the formula $L_1 M''(L_3)_x(L_4)_y(L_5)_{z'}$ wherein M'' is selected from tungsten (W) or chromium (Cr), $L_1$ is selected from substituted cyclopentadienyl, cycloheptadienyl, pentadienyl, pyrrolyl, imidazolyl, pyrazolyl and boratabenzyl, $L_3$ is selected from substituted or unsubstituted nitrosyls, $L_4$ is selected from substituted or unsubstituted carbonyls, phosphines, amines, nitriles, alkynes and alkenes, and $L_5$ is selected from substituted or unsubstituted hydrido, halo and an alkyl groups having from 1 to 12 carbon atoms;
(ii) a compound having the formula $(L_1)_y M(CO)_x(L_6)_{z-y-x'}$ wherein M is selected from tungsten (W), tantalum (Ta), niobium (Nb), vanadium (V) or chromium (Cr), $L_1$ is selected from substituted cyclopentadienyl, cycloheptadienyl, pentadienyl, pyrrolyl, imidazolyl, pyrazolyl and boratabenzyl, and $L_6$ is selected from (i) substituted or unsubstituted hydrido, halo and an alkyl group having from 1 to 12 carbon atoms, and optionally (ii) substituted or unsubstituted nitrosyls;

(iii) a compound having the formula $L_1M'L_4(L_5)_3$ wherein M' is selected from tantalum (Ta), niobium (Nb) and vanadium (V), $L_1$ is selected from substituted cyclopentadienyl, cycloheptadienyl, pentadienyl, pyrrolyl, imidazolyl, pyrazolyl and boratabenzyl, $L_4$ is selected from substituted or unsubstituted carbonyls, phosphines, amines, nitriles, alkynes and alkenes, and $L_5$ is selected from substituted or unsubstituted hydrido, halo and an alkyl groups having from 1 to 12 carbon atoms;

(iv) a compound having the formula $(L_1)_yM(NO)_{x''}(L_7)_{z-y-x''}$ wherein M is selected from tungsten (W), tantalum (Ta), niobium (Nb), vanadium (V) or chromium (Cr), $L_1$ is selected from substituted cyclopentadienyl, cycloheptadienyl, pentadienyl, pyrrolyl, imidazolyl, pyrazolyl and boratabenzyl, and $L_7$ is selected from (i) substituted or unsubstituted hydrido, halo and an alkyl group having from 1 to 12 carbon atoms, and optionally (ii) substituted or unsubstituted carbonyl, phosphino, amino, alkenyl, alkynyl, nitrile and isonitrile; and (v) a compound having the formula $L_1M'(L_3)_2L_5$ wherein M' is selected from tantalum (Ta), niobium (Nb) and vanadium (V), $L_1$ is selected from substituted cyclopentadienyl, cycloheptadienyl, pentadienyl, pyrrolyl, imidazolyl, pyrazolyl and boratabenzyl, $L_3$ is selected from substituted or unsubstituted nitrosyls, and $L_5$ is selected from substituted or unsubstituted hydrido, halo and an alkyl groups having from 1 to 12 carbon atoms.

6. The compound of claim 1 which is selected from tris(carbonyl)(methylcyclopentadienyl)hydridotungsten, $(MeCp)W(CO)_3H$;
tris(carbonyl)(ethylcyclopentadienyl)hydridotungsten, $(EtCp)W(CO)_3H$;
tris(carbonyl)(pentamethylcyclopentadienyl)hydridotungsten, $Cp*W(CO)_3H$;
tris(carbonyl)(methylcyclopentadienyl)methyltungsten, $(MeCp)W(CO)_3CH_3$;
tris(carbonyl)(ethylcyclopentadienyl)methyltungsten, $(EtCp)W(CO)_3CH_3$;
tris(carbonyl)(pentamethylcyclopentadienyl)methyltungsten, $Cp*W(CO)_3CH_3$;
tris(carbonyl)(methylcyclopentadienyl)ethyltungsten, $(MeCp)W(CO)_3C_2H_5$;
tris(carbonyl)(ethylcyclopentadienyl)ethyltungsten, $(EtCp)W(CO)_3C_2H_5$;
tris(carbonyl)(pentamethylcyclopentadienyl)ethyltungsten, $Cp*W(CO)_3C_2H_5$;
tris(acetonitrile)(methylcyclopentadienyl)hydridotungsten, $(MeCp)W(NCCH_3)_3H$;
tris(acetonitrile)(ethylcyclopentadienyl)hydridotungsten, $(EtCp)W(NCCH_3)_3H$;
tris(acetonitrile)(pentamethylcyclopentadienyl)hydridotungsten, $Cp*W(NCCH_3)_3H$;
tris(carbonyl)(2,4-dimethylpentadienyl)hydridotungsten, $((CH_3)_2C_5H_5)W(CO)_3H$;
tris(carbonyl)(2,5-dimethylpyrrolyl)hydridotungsten, $((CH_3)_2C_4H_2N)W(CO)_3H$;
methylcyclopentadienylbis(nitrosyl)hydridotungsten, $(MeCp)W(NO)_2H$;
ethylcyclopentadienylbis(nitrosyl)hydridotungsten, $(MeCp)W(NO)_2H$;
pentamethylcyclopentadienylbis(nitrosyl)hydridotungsten, $Cp*W(NO)_2H$;
methylcyclopentadienylbis(nitrosyl)methyltungsten, $(EtCp)W(NO)_2CH_3$;
ethylcyclopentadienylbis(nitrosyl)methyltungsten, $(MeCp)W(NO)_2CH_3$;
pentamethylcyclopentadienylbis(nitrosyl)methyltungsten, $Cp*W(NO)_2CH_3$;
methylcyclopentadienylbis(nitrosyl)ethyltungsten, $(EtCp)W(NO)_2C_2H_5$;
ethylcyclopentadienylbis(nitrosyl)ethyltungsten, $(MeCp)W(NO)_2C_2H_5$;
pentamethylcyclopentadienylbis(nitrosyl)ethyltungsten, $Cp*W(NO)_2C_2H_5$;
cycloheptadienylbis(nitrosyl)hydridotungsten, $(C_7H_9)W(NO)_2H$;
(2,4-dimethylpentadienyl)bis(nitrosyl)hydridotungsten, $((CH_3)_2C_5H_5)W(NO)_2H$;
(2,5-dimethylpyrrolyl)bis(nitrosyl)hydridotungsten, $((CH_3)_2C_4H_2N)W(NO)_2H$;
methylcyclopentadienylnitrosylbis(hydrido)tungsten, $(MeCp)W(NO)H_2$;
ethylcyclopentadienylnitrosylbis(hydrido)tungsten, $(EtCp)W(NO)H_2$;
pentamethylcyclopentadienylnitrosylbis(hydrido)tungsten, $Cp*W(NO)H_2$;
methylcyclopentadienylnitrosylbis(methyl)tungsten, $(MeCp)W(NO)(CH_3)_2$;
ethylcyclopentadienylnitrosylbis(methyl)tungsten, $(EtCp)W(NO)(CH_3)_2$;
pentamethylcyclopentadienylnitrosylbis(methyl)tungsten, $Cp*W(NO)(CH_3)_2$;
methylcyclopentadienylnitrosylbis(ethyl)tungsten, $(MeCp)W(NO)(C_2H_5)_2$;
ethylcyclopentadienylnitrosylbis(ethyl)tungsten, $(EtCp)W(NO)(C_2H_5)_2$;
pentamethylcyclopentadienylnitrosylbis(ethyl)tungsten, $Cp*W(NO)(C_2H_5)_2$;
cycloheptadienylnitrosylbis(ethyl)tungsten, $(C_7H_9)W(NO)(C_2H_5)_2$;
2,4-dimethylpentadienylnitrosylbis(ethyl)tungsten, $((CH_3)_2C_5H_5)W(NO)(C_2H_5)_2$; and
2,5-dimethylpyrrolylnitrosylbis(ethyl)tungsten, $((CH_3)_2C_4H_2N)W(NO)(C_2H_5)_2$.

7. A process for producing the compound of claim 1, which process comprises reacting a metal halide, a salt and a reducing agent in the presence of a first solvent and under reaction conditions sufficient to produce an intermediate reaction material, and reacting said intermediate reaction material with a base material in the presence of a second solvent and under reaction conditions sufficient to produce said compound.

8. The process of claim 7 wherein said metal halide comprises tungsten hexachloride, chromium hexachloride, tantalum pentachloride, niobium pentachloride or vanadium pentachloride; said salt comprises sodium cyclopentadiene, potassium cyclopentadiene, lithium cyclopentadiene or magnesocene; said reducing agent comprises sodium bis(2-methoxyethoxy)aluminum dihydride, sodium borohydride or lithium aluminum hydride; said first solvent comprises dimethoxyethane (DME), toluene or mixtures thereof; said intermediate reaction material is selected from $Li[(EtCp)W(CO)_3]$, $Na[(EtCp)W(CO)_3]$, and $PPN[(2,5-dimethylpyrrolyl)W(CO)_3]$; said base material comprises sodium hydroxide, potassium hydroxide or ethyl acetate; and said second solvent comprises toluene, hexane or mixtures thereof.

9. A method for producing a film, coating or powder by decomposing the-organometallic precursor compound of claim 1, thereby producing said film, coating or powder.

10. The method of claim 9 wherein the decomposing of said organometallic precursor compound of claim 1 is thermal, chemical, photochemical or plasma-activated.

11. The method of claim 9 wherein said organometallic precursor compound of claim 1 is vaporized and the vapor is directed into a deposition reactor housing a substrate.

12. The method of claim 11 wherein said substrate is comprised of a material selected from the group consisting of a metal, a metal silicide, a semiconductor, an insulator and a barrier material.

13. The method of claim 11 wherein said substrate is a patterned wafer.

14. The method of claim 9 wherein said film, coating or powder is produced by chemical vapor deposition, atomic layer deposition, plasma assisted chemical vapor deposition or plasma assisted atomic layer deposition.

15. The method of claim 9 wherein tungsten, tungsten nitride, tungsten carbide, or tungsten carbonitride is deposited on said substrate.

16. A method for processing a substrate in a processing chamber, said method comprising (i) introducing the organometallic precursor compound of claim 1 into said processing chamber, (ii) heating said substrate to a temperature of about 100° C. to about 400° C., and (iii) dissociating said organometallic precursor compound of claim 1 in the presence of a processing gas to deposit a metal layer on said substrate.

17. The method of claim 16 wherein tungsten, tungsten nitride, tungsten carbide, or tungsten carbonitride is deposited on said substrate.

18. The method of claim 16 wherein said metal layer is deposited on said substrate by chemical vapor deposition, atomic layer deposition, plasma assisted chemical vapor deposition or plasma assisted atomic layer deposition.

19. The method of claim 16 wherein said processing gas is selected from hydrogen, argon, helium, or combinations thereof.

20. The method of claim 16 wherein dissociating the organometallic precursor compound of claim 1 further comprises generating a plasma at a power density between about 0.6 Watts/cm$^2$ and about 3.2 Watts/cm$^2$.

21. The method of claim 16 further comprising exposing the deposited metal layer to a plasma generated at a power density between about 0.6 Watts/cm$^2$ and about 3.2 Watts/cm$^2$.

22. The method of claim 16 furthering comprising depositing a second metal layer on the metal layer.

23. The method of claim 22 wherein the second metal layer comprises copper and is deposited by an electroplating technique.

24. A method for forming a metal material on a substrate from the organometallic precursor compound of claim 1, said method comprising vaporizing said organometallic precursor compound of claim 1 to form a vapor, and contacting the vapor with the substrate to form said metal material thereon.

25. The method of claim 24 wherein the metal material comprises tungsten, tungsten nitride, tungsten carbide, or tungsten carbonitride.

26. The method of claim 24 wherein the substrate comprises a microelectronic device structure.

27. The method of claim 24 wherein tungsten, tungsten nitride, tungsten carbide, or tungsten carbonitride is deposited on said substrate, and the substrate is thereafter metallized with copper or integrated with a ferroelectric thin film.

28. A method of fabricating a microelectronic device structure, said method comprising vaporizing the organometallic precursor compound of claim 1 to form a vapor, contacting said vapor with a substrate to deposit a metal-containing film on the substrate, and thereafter metallizing the substrate with copper or integrating it with a ferroelectric thin film.

29. The method of claim 28 wherein the metal-containing film comprises tungsten, tungsten nitride, tungsten carbide, or tungsten carbonitride.

* * * * *